United States Patent
Abdulhalim

(10) Patent No.: US 10,048,200 B2
(45) Date of Patent: Aug. 14, 2018

(54) OPTICAL SENSOR BASED WITH MULTILAYERED PLASMONIC STRUCTURE COMPRISING A NANOPOROUS METALLIC LAYER

(71) Applicant: PHOTONICSYS LTD., Wahat Alsalam-Neveh Shalom (IL)

(72) Inventor: Ibrahim Abdulhalim, Wahat Alsalam-Neveh Shalom (IL)

( * ) Notice: Subject to any disclaimer, the term of this patent is extended or adjusted under 35 U.S.C. 154(b) by 247 days.

(21) Appl. No.: 14/909,933

(22) PCT Filed: Jun. 10, 2014

(86) PCT No.: PCT/IL2014/050522
§ 371 (c)(1),
(2) Date: Feb. 3, 2016

(87) PCT Pub. No.: WO2015/019341
PCT Pub. Date: Feb. 12, 2015

(65) Prior Publication Data
US 2016/0178516 A1   Jun. 23, 2016

Related U.S. Application Data

(60) Provisional application No. 61/862,018, filed on Aug. 4, 2013.

(51) Int. Cl.
*G01N 21/55* (2014.01)
*G01N 21/552* (2014.01)
(Continued)

(52) U.S. Cl.
CPC ......... *G01N 21/554* (2013.01); *G01N 29/022* (2013.01); *G01N 29/2418* (2013.01);
(Continued)

(58) Field of Classification Search
CPC ............. G01N 21/554; G01N 29/2418; G01N 29/022; G01N 2201/0612;
(Continued)

(56) References Cited

U.S. PATENT DOCUMENTS

| 4,844,613 A | 7/1989 | Batchelder |
|---|---|---|
| 6,801,317 B2 | 10/2004 | Hofmann |

(Continued)

FOREIGN PATENT DOCUMENTS

| EP | 2372343 A1 | 10/2011 |
|---|---|---|
| KR | 2012/0049685 | 5/2012 |

(Continued)

OTHER PUBLICATIONS

Shalabney et al, "Metallic Nanosculptured Thin Films for Biosensing Applications using Surface Plasmon Resonance and Enhanced Spectroscopies", 2012 IEEE 27th Convention of Electrical and Electronics Engineers in Israel, pp. 1-5.*

(Continued)

*Primary Examiner* — Hina F Ayub
*Assistant Examiner* — Amanda Merlino
(74) *Attorney, Agent, or Firm* — Roy Gross; The Roy Gross Law Firm, LLC

(57) ABSTRACT

The invention is a SPR sensor that comprises a multi-layered plasmonic structure on a substrate for sensing. The SPR sensor has an enhanced figure of merit and lower limit of detection (system noise divided by the sensitivity) by at least two orders of magnitude than prior art SPR sensors. The plasmonic structure of the invention comprises a Nanostructured Porous Metal Layer (NPML) and at least one of: (a) buried dielectric layer under the nano-porous metal layer; (b) a nano-dimensional high index layer on top of the metal layer; and (c) a molecular layer for bio-functionalization adjacent to an analyte layer. The invention also encompasses (Continued)

many embodiments of measuring systems that comprise the SPR sensors of the invention with improved signal to noise ratio.

18 Claims, 13 Drawing Sheets

(51) Int. Cl.
G01N 29/02 (2006.01)
G01N 29/24 (2006.01)
B82Y 30/00 (2011.01)
G01N 21/64 (2006.01)
G01N 21/65 (2006.01)
G01N 21/77 (2006.01)
B82Y 20/00 (2011.01)

(52) U.S. Cl.
CPC ............... B82Y 20/00 (2013.01); B82Y 30/00 (2013.01); G01N 21/648 (2013.01); G01N 21/658 (2013.01); G01N 21/7703 (2013.01); G01N 2021/7709 (2013.01); G01N 2021/7776 (2013.01); G01N 2201/068 (2013.01); G01N 2201/0612 (2013.01); G01N 2201/0633 (2013.01); G01N 2201/06113 (2013.01); Y10S 977/954 (2013.01)

(58) Field of Classification Search
CPC ..... G01N 2201/0633; G01N 2201/068; G01N 2201/06113; G01N 21/658; G01N 21/648; G01N 21/7703; G01N 2021/7776; G01N 2021/7709; Y10S 977/954; B82Y 20/00; B82Y 30/00
USPC ........................................................ 356/445
See application file for complete search history.

(56) References Cited

U.S. PATENT DOCUMENTS

2006/0109471 A1   5/2006  Lin et al.
2009/0040524 A1*  2/2009  Joung ................... G01N 21/553
                                               356/445
2009/0026307 A1   10/2009 Albert et al.

FOREIGN PATENT DOCUMENTS

WO   2004/074819       9/2004
WO   2007/090666 A1    8/2007
WO   2008/063139       5/2008
WO   2012/111001       8/2012

OTHER PUBLICATIONS

International Search Report from a counterpart foreign application—PCT/IL2014/050522—5 pages, dated Oct. 5, 2014.
Written Opinion of the International Searching Authority from a counterpart foreign application—PCT/IL2014/050522—5 pages, dated Oct. 5, 2014.
Keathley et al., Nano-gap-enhanced surface plasmon resonance sensors, plasmonics, vol. 7, Issue 1, Mar. 2012, 59-69.
Lim J. et al., Composite magnetic-plasmonic nanoparticles for biomedicine: Manipulation and imaging, Nano Today, vol. 8, Issue 1, Feb. 2013, pp. 98-113.
Supplementary European Search Report for EP 1483 5171—communication from a foreign patent office in a counterpart foreign application—; dated Feb. 27, 2017; 10 pages.
Abdulhalim I., Enhancing the sensitivity of surface-plasmon resonance sensors, SPIE Newsroom Jan. 21, 2009 (3 pages).
Shalabney A., et al., Sensitivity of surface plasmon resonance sensors based on metallic columnar thin films in the spectral and angular interrogations, sensors and actuators B: Chemical, vol. 159, Issue 1, Nov. 28, 2011, pp. 201-212 (13 pages).
Lahav A. et al., Surface plasmon resonance sensor with enhanced sensitivity using nano-top dielectric layer, Journal of nano-photonics, vol. 3, Issue 1, Jan. 21, 2009, pp. 1-14 (14 pages).
Hastings J. et al., Optimal self-referenced sensing using long and short range surface plasmons, Optics Express, vol. 15, issue 26, Dec. 24, 2007, 17661-17672, Dec. 12, 2007 (12 pages).
Patskovsky S. et al., Silicon-based surface plasmon resonance sensing with two surface plasmon polariton modes, Applied Optics, vol. 42, Issue 34, Dec. 1, 2003, pp. 6905-6909 (5 pages).
Lee K.S. et al., Surface plasmon resonance biosensing based on target-responsive mobility switch of magnetic nanoparticles under magnetic fields, Journal of Materials Chemistry, vol. 21, Issue 13, Feb. 21, 2011 (7 pages).
Wang Y. et al., Magnetic Nanoparticle-enhanced Biosensor based on grating-coupled surface plasmon resonance, Analytical Chemistry, vol. 83, Aug. 15, 2011, pp. 6202-6207 (6 pages).
He L. et al., Colloidal Au-Enhanced surface plasmon resonance for ultrasensitive detection of DNA hybridization, J. Am. Chem. Soc. vol. 122, Issue 38, Sep. 27, 2000, pp. 9071-9077 (7 pages).
Heinz Raether, Surface Plasmons on Smooth and Rough Surfaces and on Gratings, Springer Verlag 1988 (1 page).
K. D. Kihm, "Surface plasmon resonance reflectance imaging technique for near-field (~100 nm) fluidic aharacterization" Experiments in Fluids 48, 547-564 (2010) (18 pages).
A. D. Taylor, J. Ladd, J. Homola, and S. Jiang, "Surface Plasmon Resonance (SPR) Sensors for the Detection of Bacterial Pathogens," in Principles of Bacterial Detection: Biosensors, Recognition Receptors and Microsystems (Springer New York, 2008), pp. 83-108 (28 pages).
R. B. M. Schasfoort, and A. J. Tudos, eds. Handbook of Surface Plasmon Resonance (Royal Society of Chemistry, Cambridge, 2008). (4 pages).
A. Karabchevsky, S. Karabchevsky, and I. Abdulhalim, Fast surface plasmon resonance imaging sensor using Radon transform, Sensors and Actuators B: Chemical, 155, 361-365 (2011) (6 pages).
A. Karabchevsky, S. Karabchevsky, and I. Abdulhalim, Nano-precision algorithm for surface plasmon resonance determination from images with low contrast for improved sensor resolution, J. NanoPhotonics, 5, 051813 1-12 (2011). DOI: 10.1117/1.3598138 (13 pages).
Amit Lahav, Mark Auslender and I. Abdulhalim, Sensitivity enhancement of guided wave surface plasmon resonance sensors, Opt.Lett. 33, 2539-2541 (2008) (3 pages).
Amit Lahav, Atef Shalabney, I. Abdulhalim, Surface plasmon resonance sensor with enhanced sensitivity using nano-top dielectric layer, Journal of Nano-photonics 3, 031501 (2009) (14 pages).
Atef Shalabney and I. Abdulhalim, Figure of merit enhancement of surface plasmon resonance sensors in the spectral interrogation, Optics Letters 37, 1175-1177 (2012) (3 pages).
Atef Shalabney, C. Khare, B. Rauschenbach, and I. Abdulhalim, Sensitivity of surface plasmon resonance sensors based on metallic columnar thin films in the spectral and angular interrogations, Sensors and Actuators B: Chemical, 159, 201-212 (2011) (13 pages).
Y. Y. Shevchenko and J. Albert, "Plasmon resonances in gold-coated tilted fiber Bragg gratings," Opt. Lett. 32, 211-213 (2007) (3 pages).
T. Allsop, R. Neal, S. Rehman, D. J. Webb, D. Mapps, and I. Bennion, "Generation of infrared surface plasmon resonances with high refractive index sensitivity utilizing tilted fiber Bragg gratings," Applied Optics 46, 5456-5460 (2007) (5 pages).
L. Shao, Y. Shevchenko, and J. Albert, "Intrinsic temperature sensitivity of tilted fiber Bragg grating based surface plasmon resonance sensors," Opt. Express 18, 11464-11471 (2010) (8 pages).
C. Caucheteur, Y. Shevchenko, L. Shao, M. Wuilpart, and J. Albert, "High resolution interrogation of tilted fiber grating SPR sensors from polarization properties measurement," Opt. Express 19, 1656-1664 (2011) (9 pages).

(56) References Cited

OTHER PUBLICATIONS

Valérie Voisin, Christophe Caucheteur, Patrice Mégret, and Jacques Albert, "Interrogation technique for TFBG-SPR refractometers based on differential orthogonal light states," Applied Optics 50, 4257-4261 (2011) (5 pages).

I. Abdulhalim,—Analytic propagation matrix method for linear optics of arbitrary biaxial layered media, J. Opt. A, 1 (5) (646-653) 1999 (8 pages).

O. Aharon, I. Abdulhalim, Liquid crystal wavelength independent continuous polarization rotator, Optical Engineering 49, 034002-4p (2010) (4 pages).

I. Abdulhalim, Plasmonic Sensing using Metallic Nano-Sculptured Thin Films, Invited review article, Small, 2014, DOI: 10.1002/smll.201303181 (16 pages).

Keathley P., "Design and analysis of nano-gap enhanced surface plasmon resonance sensors". (2009) University of Kentucky master's theses. XP055341228 (102 pages).

Shalabney A. et al., "Sensitivity-enhancement methods for surface plasmon sensors". Laser & photonics reviews 2011, vol. 5(4) pp. 591-601, XP 055006811 (36 pages).

Md. Islam S. et al., "Sensitivity analysis of a sub-wavelength localized surface plasmon resonance graphene biosensor". Complex medical engineering (CME) 2012, ICME International conference on IEEE, pp. 490-494. XP 032222834 (5 pages).

\* cited by examiner

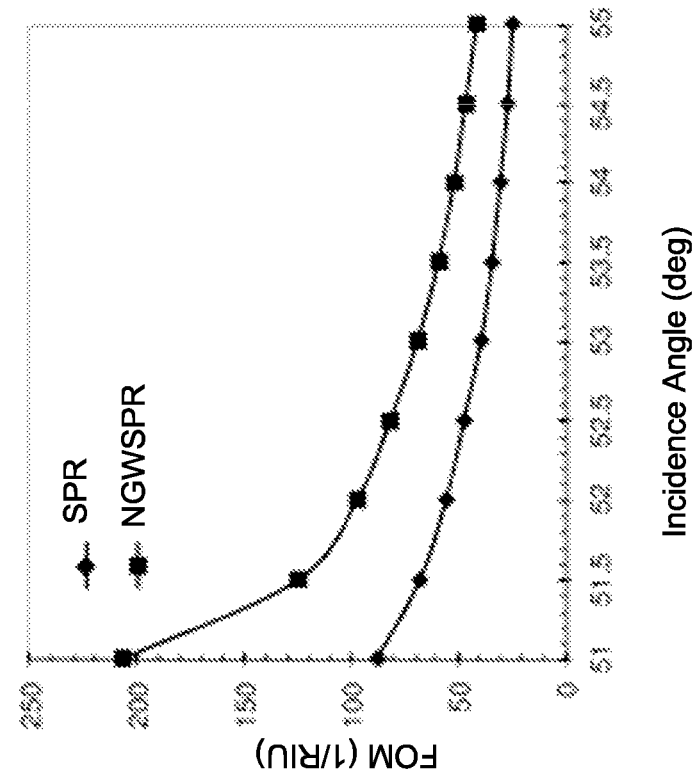
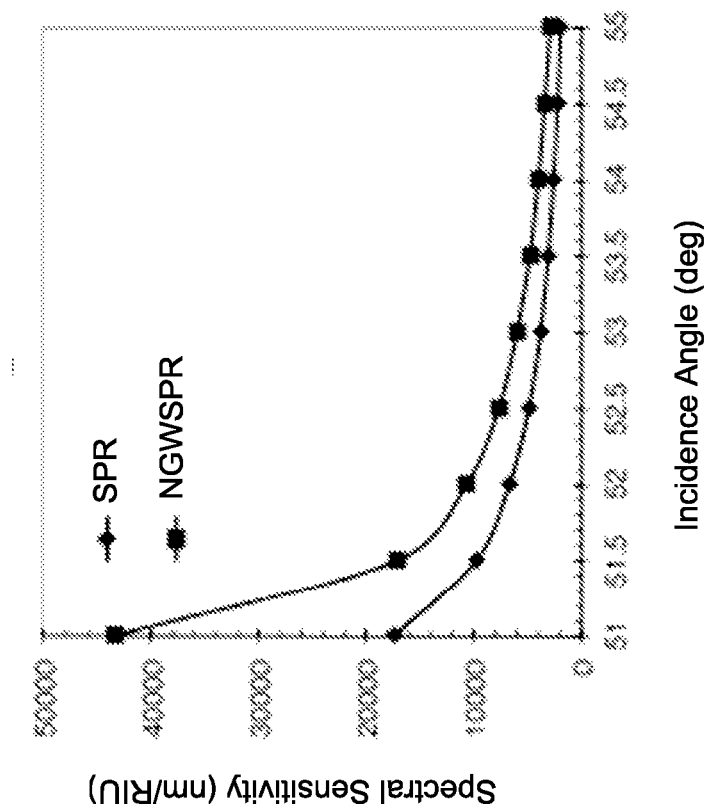
Fig. 5b
Fig. 5a

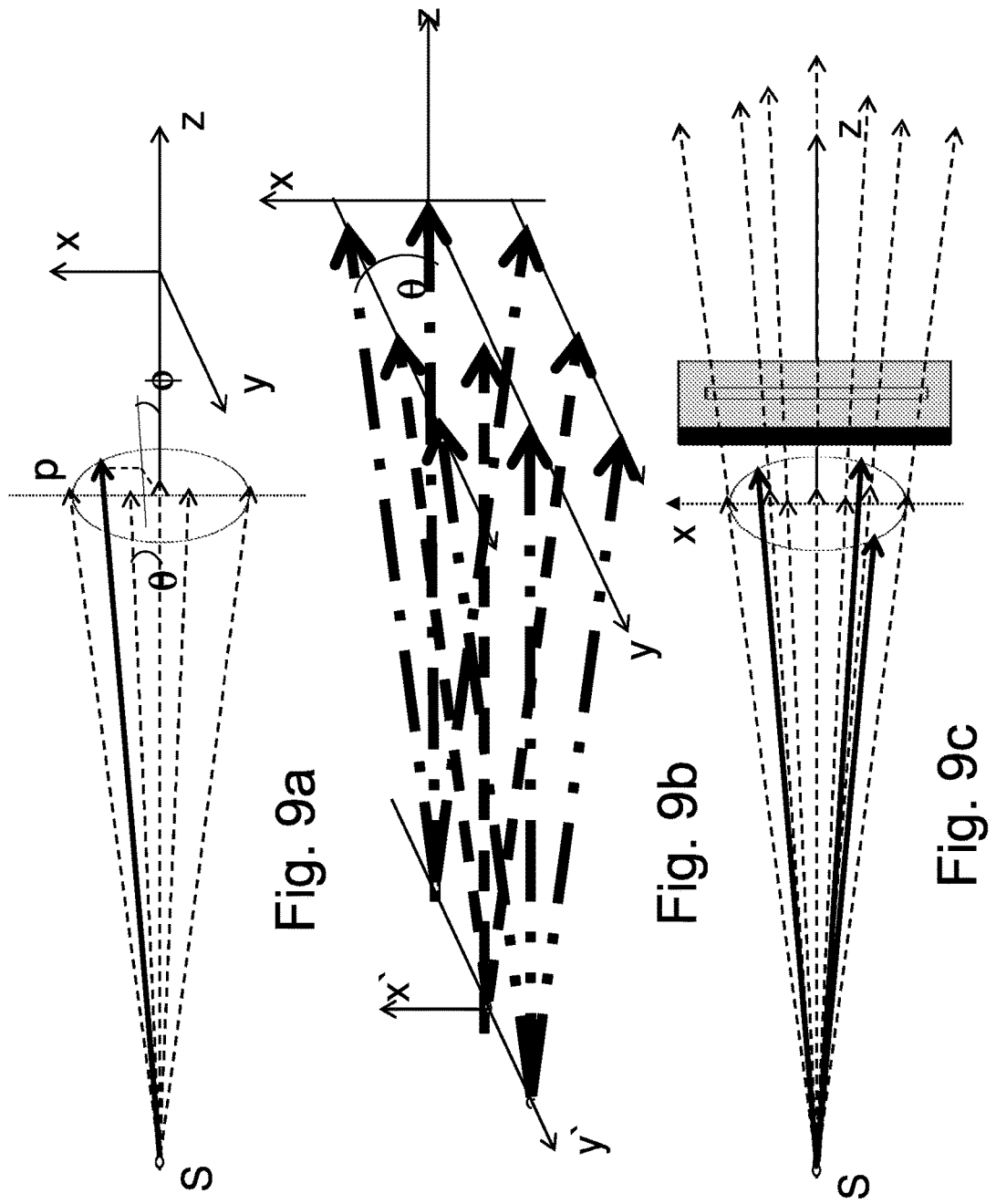

OPTICAL SENSOR BASED WITH MULTILAYERED PLASMONIC STRUCTURE COMPRISING A NANOPOROUS METALLIC LAYER

FIELD OF THE INVENTION

The invention is from the field of quantum electromagnetic (EM) phenomenon. Specifically the invention is from the field of Surface Plasmon Resonance (SPR).

BACKGROUND OF THE INVENTION

Publications and other reference materials referred to herein are numerically referenced in the following text and respectively grouped in the appended Bibliography which immediately precedes the claims.

Surface Plasmon Resonance (SPR) is a quantum electromagnetic (EM) phenomenon arising from the interaction of light with free electrons at a metal-dielectric interface emerging as a longitudinal EM wave in a two dimensional gas of charged particles such as free electrons in metals. Under certain conditions the energy carried by the photons is transferred to collective excitations of free electrons, called surface plasmons (SPs), at that interface. This transfer of energy occurs only at a specific resonance wavelength of light when the momentum of the photon matches that of the plasmon[1]. The SPs excited are strongly localized across the interface, and may be considered classically as EM surface waves that propagate along the interface and decay exponentially with distance normal to the interface. SPR is responsible for a dip in reflectance at the specific wavelength, the dip resulting from the absorption of optical energy in the metal. Since SP waves are tightly bound to metal-dielectric interfaces penetrating around 10 nm into the metal (the so-called skin-depth) and typically more than 100 nm into the dielectric (depending on the wavelength), they concentrate EM wave in a region that is considerably smaller than their wavelength.

There are two main types of SPs with respect to their propagation characteristics along the interface: extended or propagating and localized. The propagating SP is considered as more classical since it has been known for a longer time. However the latest advancements in nanotechnology have made the fabrication of structures with nm scale features feasible, thus the localized SPR has become a subject of immense interest during the last two decades. Localized SPs are excited in metallic structures with lateral dimensions less than half the wavelength of the exciting EM wave. A third type of plasmon may be mentioned called long range SPR (LRSPR) which exists in thin metal films or strips characterized by low attenuation and travelling along the surface for distances up to few mm in the visible or even a few cm in the infrared. This latter type might have applications in active photonic components and highly sensitive sensors particularly of large biological entities such as cells.

In the case of propagating SPR (PSPR), plasmons propagate along the interface between metal and dielectric for distances on the order of microns to tens and even hundreds of microns and decay evanescently in the z direction (see FIGS. 1a to 1f normal to the interface with 1/e decay length on the order of half the wavelength (~200 nm for wavelengths in the visible range). The interaction between the metal surface-confined EM waves and the molecular layer of interest leads to shifts in the plasmon resonance, which can be observed in three main modes: (a) angle resolved mode, (b) wavelength shift mode, and (c) imaging mode. In the first two modes, one measures the reflectivity of light from the metal surface as a function of either wavelength (at constant incidence angle) or as a function of incidence angle (at constant wavelength). The third mode uses light of both constant wavelength and incidence angle to interrogate a two-dimensional region of the sample, mapping the reflectivity of the sample as a function of position. In each of these modes one can measure intensity, phase or polarization change.

PSPR biosensors have been widely applied in a diverse range of fields, including molecular recognition, and disease immunoassays, etc. Even though conventional SPR biosensors are more sensitive than other label-free devices, they are still unable to achieve the direct detection of small molecular (few hundreds of Daltons) interactions or low molecular concentrations (physiological concentration) on the surface of the biosensor. Consequently, various proposals have been developed to enhance the sensitivity or resolution of biosensors by using different SPR modes or detection methods. Also, various localized SPR (LSPR) biosensors have been proposed which employ the strong UV-Vis absorption band of the metal nanoparticles to yield an area mass detection limit of 100-1000 pg/mm$^2$. However, this detection capability is poorer than that of conventional PSPR biosensors by an order of 10-100 times.

FIG. 1a to FIG. 1f schematically show several techniques for enhancing the wave vector to excite the SP wave. FIG. 1a shows prism coupling on the top of the metallic film, in which the wave vector is enhanced by the prism refractive index. This method is known as the Kretschmann configuration. In FIG. 1a are shown the incident light 2, reflected light 4, metal film 6, analyte 32, and prism 10. The field distribution is symbolically shown as 12.

FIG. 1b shows prism coupling with a thin gap (filled with analyte) between bulk metal and the prism in what is known as the Otto configuration. In this configuration the wave vector is enhanced by the prism refractive index and the coupling occurs via evanescent waves since the air gap is thinner than the light penetration depth. In FIG. 1b are shown the incident light 2, reflected light 4, air gap 14, bulk metal 16, prism 10 and the field distribution 12.

FIG. 1c shows coupling through a diffraction grating, in which the wave vector is enhanced by the diffraction. In FIG. 1c are shown incident light 2, reflected light 4, metal film 6, analyte 32, the field distribution 12 and diffraction grating 26.

FIG. 1d shows waveguide coupling. In FIG. 1d are shown metal film 6, analyte 32, the field distribution 12, waveguide 18, and the transmitted light 20.

FIG. 1e shows fiber coupling. Shown in this figure are metal film 6, analyte 32, and fiber 22. FIG. 1f shows nano probe coupling. Shown in this figure are bulk metal 16, the field distribution 12, and a scanning near field optical microscope (SNOM) probe 24. In FIG. 1E and FIG. 1F the coupling mechanism is based on the evanescent waves either within a waveguide interface or in the near field of a scanning microscope.

Perturbation in the substrate refractive index (dielectric 32) causes a change in the incident light wave vector and consequently a shift in the resonance wavelength for a fixed incidence angle or a shift in the incidence angle for a fixed wavelength because the wave vector along the interface is:

$$k_x = 2\pi n_p \sin \theta_p / \lambda.$$

The excitation of plasmons by transverse magnetic (TM) polarized coherent light in the KR configuration requires a prism [1], which matches between the wave vector of the incidence light along the interface $k_x = n_p k_0 \sin\theta_p$, where $k_0 = 2\pi/\lambda$ and the k vector of the surface plasmon $k_{sp} = k_0 (\varepsilon_m \varepsilon_a (\varepsilon^m + \varepsilon_a))^{1/2}$:

$$\sqrt{\varepsilon_p}\sin\theta_p = \text{Re}\left\{\sqrt{\frac{\varepsilon_m \varepsilon_a}{\varepsilon_m + \varepsilon_a}}\right\} \quad (1)$$

When $\varepsilon_p$ is the dielectric constant of the prism, $\theta_p$ is defined as the propagation angle in the prism:

$$k_x = \sqrt{\varepsilon_p}\frac{\omega}{c}\sin\theta_p,$$

where c is the velocity of light in free space and ω is the radiant frequency. $\varepsilon_m$ and $\varepsilon_a$ are the complex dielectric constants of the metal and dielectric (analyte) respectively. According to equation (1) the SP can be excited at a specific angle depending on the light wavelength through the materials dispersion relation. The most popular SPR sensing scheme uses the prism coupling in the Kretschmann-Raether (KR) arrangement (FIG. 1A). In KR configuration, reflectivity is measured as a function of angle of incidence—called angular modulation (AM)—or wavelength—called wavelength modulation (WM). In AM a single wavelength, usually a collimated laser beam, is incident on the metal film through the prism while scanning through different incidence angles. The SPR dip is observed in the reflectivity versus incidence angle spectrum of a collimated beam. Although AM uses a single frequency and a collimated beam, the required scanning is problematic in particular when high accuracy and fast speed are required. Using an imaging scheme, the possibility of detecting arrays or imaging surfaces with very low contrast was demonstrated [2]. In these publications [2] however the incident beam is usually a parallel beam focused (or non-focused) on the metal-analyte surface and the surface is imaged with a lens and camera. In a less known configuration a converging [3] or diverging circular beam [4] is used which contains a wide range of angles and the divergent output beam falls on a detector array so that the SPR signal of reflectivity versus angle is obtained in a parallel manner without the need for scanning. Recently the research group led by the present inventor has published two papers [5, 6] on a SPR imaging method using diverging circular beams and a fast line detection algorithm called the Radon transform. However the disadvantages of the circular diverging beam approach are that the circular beam contains many spatial components that cannot excite an SP wave and their polarization vector contains both TE and TM components. As a result the contrast of the SPR is deteriorated, it is impossible to perform phase imaging, and multichannel imaging is more problematic.

Another important factor affecting the sensitivity is the penetration depth of the electromagnetic field inside the analyte which can be estimated from the following equation:

$$\delta_a = \frac{\lambda}{2\pi}\cdot\sqrt{\frac{\varepsilon_a + \varepsilon_{mr}}{-\varepsilon_a^2}} \quad (2)$$

For example for silver at $\lambda=1500$ nm, $\varepsilon_{mr}=-115.5$, which is much larger than $\varepsilon_a=1.769$, thus giving a penetration depth of about $\delta_a=0.96\lambda\approx1.44$ μm. For the visible range $\lambda=600$ nm, on the other hand $\varepsilon_{mr}=-14.14$, thus giving $\delta_a=0.316\lambda\approx0.19$ μm. Hence the penetration depth in the near IR (NIR) range is larger by a factor of 8 than that in the visible range, although the wavelength ratio is only 2.5.

The propagation length $L_x$ of the SP along the surface of the metal at the interface with the analyte can be estimated from:

$$L_x = \frac{\lambda}{2\pi}\cdot\frac{\varepsilon_{mr}^2}{\varepsilon_{mi}}\cdot\left[\frac{\varepsilon_a + \varepsilon_{mr}}{\varepsilon_a \cdot \varepsilon_{mr}}\right]^{3/2} \quad (3)$$

The imaginary part of silver dielectric constant at 1500 nm is $\varepsilon_{mi}=12.3$ and hence $L_x\approx72\lambda108$ μm. For the visible (λ=600 nm) on the other hand $\varepsilon_{mi}=0.96$ giving $L_x\approx11.5\lambda\approx6.9$ μm. Hence the plasmons in the IR region travel a longer range along the interface, an important fact for enhancing the sensitivity and improving the detection limit. In order to improve the propagation length and the penetration depth further the long range SPR (LRSPR) configuration is introduced in which an additional dielectric layer buried underneath the metal layer is added with refractive index close to that of the analyte. In this mode two SPR dips are obtained where one is excited at the buried layer-metal interface and one at the metal-analyte interface. The former is not sensitive to the variations in the analyte refractive index and therefore can be used as a reference dip to compensate for temperature fluctuations or other system noise effects. The latter dip however exhibits enhanced sensitivity to the analyte refractive index changes due to the increase in the penetration depth and the propagation length.

It is a purpose of the present invention to provide SPR sensors that have an enhanced figure of merit and lower limit of detection than prior art SPR sensors.

Further purposes and advantages of this invention will appear as the description proceeds.

SUMMARY OF THE INVENTION

In a first aspect the invention is a sensor comprised of a multilayered plasmonic structure comprising a nano-porous metallic layer and at least one of the following layers:

a buried dielectric layer under the nanoporous metal;

a nano dimensional high refractive index dielectric layer on top of the nanoporous metallic layer; and a molecular layer for bio-functionalization on the interface of the multilayered structure with an analyte.

In embodiments of the sensor of the invention the thickness of the nanoporous metallic layer is 15 nm-70 nm.

In embodiments of the sensor of the invention the porosity of the nanoporous metallic layer is between 1% and 35%.

In embodiments of the sensor of the invention the refractive index of the buried dielectric layer is approximately equal to that of the material to be sensed.

In embodiments of the sensor of the invention the thermo-optic coefficient of the buried dielectric layer is the same as that of the material to be sensed.

In a second aspect the invention is a method of using the sensor of the first aspect to:

i. determine the refractive index of a material; or ii. determine the presence and quantity of biological or chemical entities in thin film form or in an analyte; or iii. make displacement and surface profiling measurements; or
iv. to measure defocusing of an optical system;
the method comprising:
   a. providing an optical setup adapted to irradiate an analyte covered sensor of the first aspect of the invention with an input beam comprising TM polarized light;
   b. measuring the resonance wavelength or incidence angle of the resonant reflection dips of the plasmon excited at the plasmonic structure-analyte interface relative to the resonance wavelength or to the incidence angle of the resonant reflection dips of the plasmon excited at the buried dielectric layer—metal interface or relative to a reference material layer residing on top of the sensor—analyte interface and occupying part of its surface.

In embodiments of the method of the invention the optical thickness of the buried dielectric layer of the sensor is between one half the wavelength and a few times the wavelength of the incident light inside the layer.

In embodiments of the method of the invention the optical thickness of the nano dimensional high refractive index dielectric layer is less than the cutoff for exciting guided modes in the top nano-dimensional layer.

In embodiments of the method of the invention the optical setup comprises one of the following:
   i. a quasi-monochromatic light source;
   ii. a wideband light source;
   iii. a multiple color light source; and
   iv. a tunable light source adapted to provide quasi monochromatic light at multiple wavelengths serially.

In embodiments of the method of the invention the optical setup comprises one of the following:
   i. means to obtain a uniform one dimensionally diverging beam in the plane of incidence of the input beam; and
   ii. means to obtain a uniform collimated beam in the plane of incidence of the input beam.

In embodiments of the method of the invention the analyte is provided in a multichannel planar structure comprised of at least two rectangular channels, each channel having a width of at least twice the plasmon propagation length and a height of at least few times the penetration depth of the electromagnetic field, wherein the channels are oriented so that the line perpendicular to the channels is perpendicular to the plane of incidence of the input beam and wherein channels containing the analyte to be inspected are separated by channels containing a material having a thermo-optic coefficient similar to that of the analyte. In these embodiments each pair of sensing and reference channels can be coated with a different top nano dimensionally thick dielectric layer of different refractive index or different thickness.

In embodiments of the method of the invention wherein the optical setup comprises a prism, the multilayer plasmonic structure of a sensor of the first aspect of the invention is created either directly on a face of the prism or is created on a transparent substrate that is attached to the prism, and an analyte to be inspected covers the sensor. In these embodiments the optical setup comprises one of the following arrangements:
   i. a collimated wideband beam of light from a light source passes through a polarizer oriented along the TM direction, is incident on and passes through the prism, is reflected from the multilayered structure of the sensor, and the reflected beam passes through the prism towards a detector, an array of detectors, or a spectrometer;
   ii. a quasi-monochromatic one dimensionally diverging beam of light from a light source passes through a polarizer oriented along the TM direction, is incident on and passes through the prism, is reflected from the multilayered structure of the sensor, and the reflected beam passes through the prism towards a detector, an array of detectors, or a camera; and
   iii. a quasi-monochromatic one dimensionally diverging beam of light from a light source passes through a first dichroic mirror, passes through a polarizer oriented along the TM direction, is incident on and passes through the prism, is reflected from the multilayered structure of the sensor, and the reflected beam passes through the prism and a second dichroic mirror towards a detector, an array of detectors, or a camera; and, simultaneously, a collimated wideband beam of light from a light source is reflected from the first dichroic mirror, passes through the same polarizer oriented along the TM direction, is incident on and passes through the prism, is reflected from the multilayered structure of the sensor, and the reflected beam passes through the prism and is reflected from the second dichroic mirror towards a detector, an array of detectors, or a spectrometer.

In embodiments of the method of the invention the input beam is coupled to the sensor of the first aspect of the invention by means of:
   i. a waveguide created on a substrate, wherein the multilayered plasmonic structure of the sensor is created on top of the waveguide;
   ii. a transparent substrate that acts as a light pipe, wherein the multilayered plasmonic structure of the sensor is created on top of the transparent substrate;
   iii. an optical fiber, wherein a portion of the core of the optical fiber is exposed by removal of the cladding and the multilayered plasmonic structure of the sensor is created directly on the side of the fiber over that portion; and
   iv. an optical fiber comprising a tilted fiber grating wherein the multilayered plasmonic structure of the sensor is created on the cladding of the fiber directly over the grating.

In embodiments of the method of the invention the optical setup comprises a light source which produces a quasi-monochromatic one dimensionally diverging input beam of light that passes through a polarizer, is incident on and passes through a prism, is reflected from the multilayered structure of the sensor, and the reflected beam passes through the prism and at least one additional optical component towards at least one camera; wherein the polarizer is oriented at 45 degrees thereby generating equally polarized TE and TM components of the input beam; and wherein the at least one optical component located between the prism and the at least one camera comprises one of the following:
   i. a polarized beam splitter, which directs each of the polarization components TE and TM to a different camera;
   ii. an analyzer; and
   iii. two non-polarizing beam splitters that direct the output beams to three different cameras and either three analyzers oriented at $-\pi/4$, $0$, $\pi/4$ degrees respectively or three analyzers oriented at $-45$ degrees and three passive waveplates providing phase retardations $0$, $\pi/2$, $\pi$, respectively.

It should also be mentioned that there are other ways of generating two equally polarized TE and TM components of the input beam which might be used, such as the use of circular polarizer instead of a linear polarizer at the input, or inserting a quarter waveplate located after the input linear polarizer.

In embodiments of the method of the invention the optical setup comprises a quasi-monochromatic diverging beam of light from a light source that passes through a polarizer oriented along the TM direction, is incident on and passes through the prism, is reflected from a first side of the multilayered structure of the sensor; the reflected beam passes through the prism towards a detector, an array of detectors, or a camera; and an enhanced emission is transmitted through the analyte and is collected using a lens and filter system from a second side of the multilayered structure of the sensor and is directed towards a detector, an array of detectors, a camera, or a spectrometer.

In embodiments of the method of the invention the input beam is reflected from a first side of the multilayered structure of the sensor towards a detector, an array of detectors, or a camera and an enhanced emission is transmitted through the analyte and is collected using a lens and filter system from a second side of the multilayered structure of the sensor and is directed towards a detector, an array of detectors, a camera, or a spectrometer.

In embodiments of the method of the invention the multilayered plasmonic structure of the sensor of the first aspect of the invention is deposited on one side of a transparent piezoelectric substrate, the nano-porous metallic layer acts as electrode to excite an acoustic wave in the piezoelectric transducer, a transparent electrode is deposited on the other side of the transparent piezoelectric substrate, and a prism, waveguide, or optical fiber coupling medium is attached using an index matching medium.

In embodiments of the method of the invention the analyte layer is contained between the multilayered plasmonic structure and another transparent cover substrate coated with a transparent electrode, thereby allowing an electric field to be applied between the transparent electrode and the nano-porous metal layer to help drag the species to be sensed towards the bio-functionalization layer.

In embodiments of the method of the invention the analyte comprises functionalized nanoparticles adapted to specifically attract the species to be detected and to bring them closer to the multilayered plasmonic structure. In these embodiments the functionalized nanoparticles can be magnetic, thereby allowing an external magnetic field to drag them towards the multilayered plasmonic structure. In these embodiments the functionalized nanoparticles can be metallic; thereby when they approach the plasmonic multilayered structure a localized plasmon is excited on their surface thus enhancing the emission and the SPR sensor sensitivity.

All the above and other characteristics and advantages of the invention will be further understood through the following illustrative and non-limitative description of embodiments thereof, with reference to the appended drawings.

BRIEF DESCRIPTION OF THE DRAWINGS

FIG. 5a shows the calculated spectral sensitivity as a function of the incidence angle for both SPR and NGWSPR structures;

FIG. 5b shows the calculated figure of merit (FOM) as a function of the incidence angle for both SPR and NGWSPR structures;

FIG. 9a illustrates the effect of a circularly diverging beam;

FIG. 9b illustrates the effect of a one dimensionally diverging beam generated from a line source;

FIG. 9c illustrates the generation of a 1D diverging beam from a circularly diverging beam using a slit aperture;

DETAILED DESCRIPTION OF EMBODIMENTS OF THE INVENTION

The invention is a SPR sensor that comprises a multi-layered plasmonic structure on a substrate for sensing that has an enhanced figure of merit and lower limit of detection (system noise divided by the sensitivity) by at least two orders of magnitude than prior art SPR sensors. The plasmonic structure of the invention comprises a Nanostructured Porous Metal Layer (NPML) and at least one of: (a) buried dielectric layer under the nano-porous metal layer; (b) a nano-dimensional high index layer on top of the metal layer; and (c) a molecular layer for bio-functionalization adjacent to an analyte layer. The invention also encompasses many embodiments of measuring systems that comprise these SPR sensors.

In this invention the use of 1-D diverging beam is utilized together with ellipso-polarimetric measurement method which helps overcoming the disadvantages of using a circularly diverging beam particularly when combined with a novel phase retardation measurement scheme. The same sensor can be used as a refractometer of a liquid or gas or even for solids deposited as thin film layers on top of the plasmonic substrate when more than one reference channel are used simultaneously.

Figure 1A:
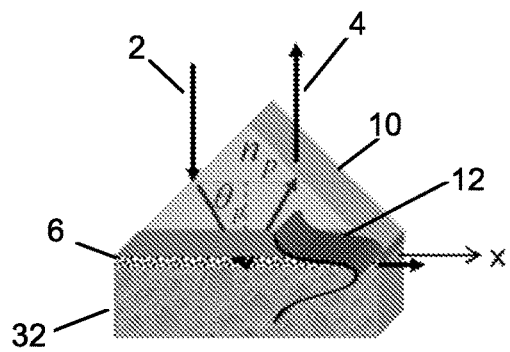
FIG. 1a to FIG. 1f schematically show several prior art techniques for enhancing the wave vector to excite the SP wave.
Figure 1B:
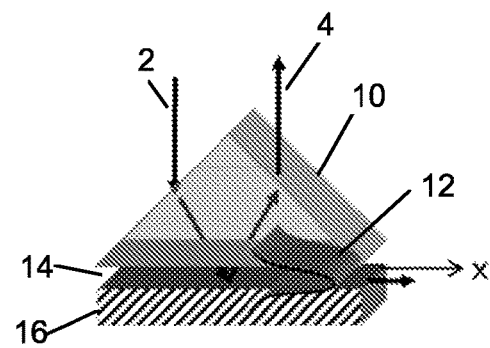
Figure 1C:
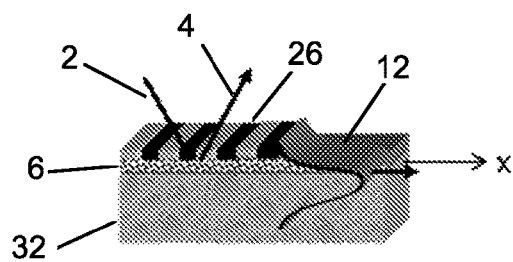
Figure 1D:
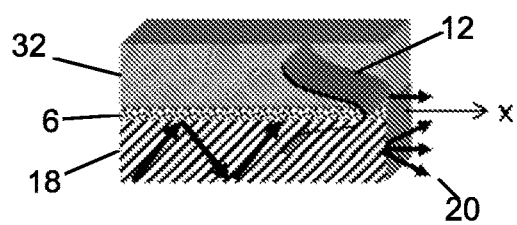
Figure 1E:
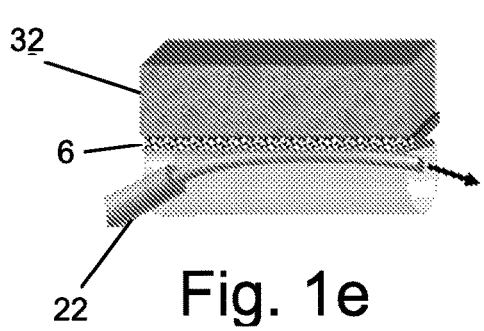
Figure 1F:
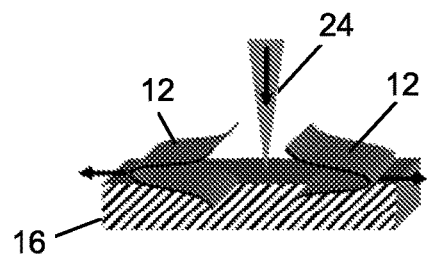
Figure 2:
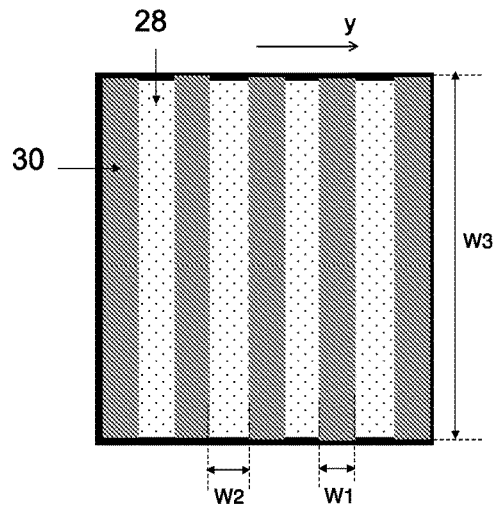
FIG. 2 schematically shows the general multi-channel analyte substrate configuration.

The Analyte Substrates:

The general multichannel analyte substrate configuration is shown schematically in FIG. 2. The substrate comprises rectangular micro-channels (at least two channels included) for the analyte material arranged such that between each two analyte micro-channels 28 there is a reference channel 30 filled with a material that has a thermo-optic coefficient that is approximately equals to that of the analyte material flowing in the neighboring channel. Each channel has a preferably different top dielectric layer of different refractive index and different thickness so that the corresponding resonance locations are separated enough from each other. Alternatively the different channels can be filled with materials having different known refractive indices. In this way the calibration of the sensor as a refractometer is simplified and is less dependent on the beam alignment.

The widths W1 of the reference material, W2 of the analyte channels containing the analytes to be inspected and the height W3 of the channels should at least be few tens of microns separated by thin walls at least few tens of microns wide and having the same height W3. The widths W1, W2 should be at least twice the propagation length of the surface Plasmon while the height W3 should be at least few times the penetration depth of the electromagnetic field inside the analyte. The micro-channels are preferably oriented so that the line perpendicular to the channels (designated y in FIG. 2) is perpendicular to the incidence plane (xz). An additional advantage of these channels is that fluids can then fill the channels by the action of the capillary forces. The reference channel of width W1 could be made from a solid material or simply be an empty channel that is filled with a fluid having a thermo-optic coefficient approximately equal to that of the analyte. Each channel can also be connected to a microtube through which the appropriate analyte to be inspected flows using a pump.

In another embodiment the analyte material in each channel can be covered on top with a transparent substrate coated with transparent electrode in conjunction with the analyte interface so that an electric field can be applied between this electrode and the nano porous metal layer. This is important in certain cases to drag the species to be detected towards the functionalization layer such as in the case of bacteria detection. The electric field to be generated is preferably non-uniform so that the species to be sensed will be dragged by the electrophoretic forces towards the plasmonic multilayered structure. The generation of non-uniform electric field can be achieved using inter-digitated electrodes structure or other means known in the art. The thickness of the analyte layer in this embodiment should be at least ten times the penetration depth of the electromagnetic field.

In another embodiment the analyte material can include functionalized nanoparticles in it to specifically catch the species to be detected and drag them towards the plasmonic multilayered structure either naturally or with the help of an applied electric or magnetic fields. The electric field to be generated is preferably non-uniform so that the nanoparticles will be dragged by the electrophoretic forces towards the plasmonic multilayered structure. For the case of magnetic field, the particles should preferably be magnetic nanoparticles. The nanoparticles are preferably of anisotropic shape so that the induced electric and magnetic forces cause them to orient in a specific direction.

Figure 3A:
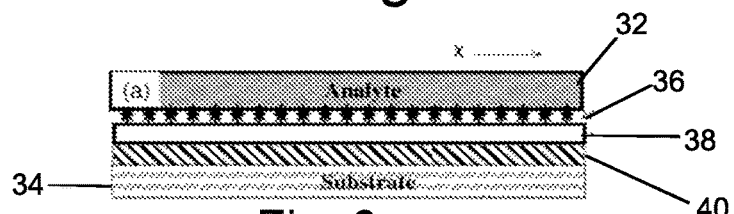
FIG. 3a to FIG. 3d schematically show cross sectional views of different embodiments of multilayered structures underneath the analyte substrate shown in FIG. 2 for prism coupling in the KR configuration.
Figure 3B:
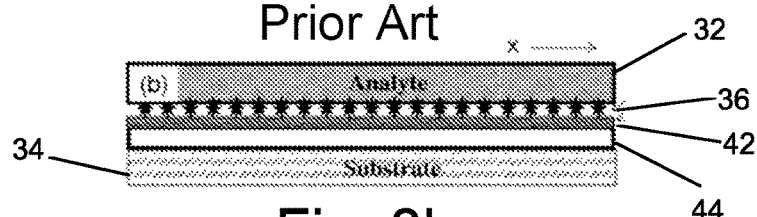
Figure 3C:
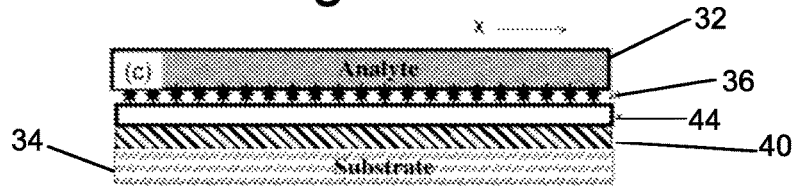
Figure 3D:
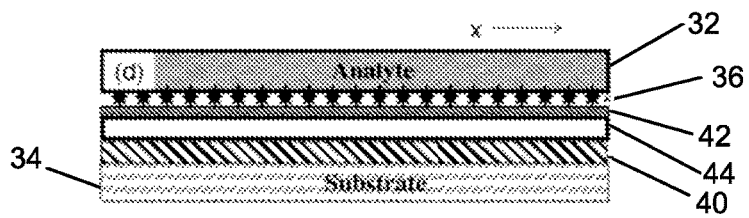

For prism coupling in the Kretschmann configuration the layer underneath the rectangular pattern shown in FIG. 2 is a multilayered structure that improves the sensitivity and figure of merit and hence also the limit of detection. FIG. 3a to FIG. 3d schematically show cross sectional views of different embodiments of multilayered structures. The multilayered structure can be deposited directly on the prism face or on a planar substrate 34 having the same refractive index as the prism to be used. An index matching fluid will then be used to attach the planar substrate to the prism. The structures shown in FIGS. 3a-3d have the following layers on top of substrate 34: (FIG. 3a) buried dielectric layer 40 under a dense metal film 38, (FIG. 3b) nanostructured porous metal film 44 with top nano-dielectric layer 42, (FIG. 3c) buried dielectric layer 40 under a porous metal film 44 and (FIG. 3d) buried dielectric layer 40 under a porous metal film 44 and top nano-dielectric layer 42. All of the structures shown in FIGS. 3a-3d comprise a substrate 34 on the bottom, an analyte 32 in a layer on the top, and a functionalization layer 36 located just below the analyte. The structure shown in FIG. 3a is known in the prior art; however its use with the diverging beam approach described herein is not known. The structures shown in FIGS. 3b to 3d are examples of the plasmonic structures of the sensors of the invention.

The nano porous metal layer (NPML), which has porosity in the range 1%-35% prepared from noble metals by several methodologies such as: (i) Glancing angle deposition technique in which the porosity can be controlled by varying the deposition angle and the substrate temperature; (ii) selective chemical etching of metal alloys such as Ag/Au alloy (such as $Ag_{68}Au_{32}$ sputtered as thin film in which the Ag may be etched using $HNO_3$ diluted solutions) and the porosity is this case is controlled by the etching time and etchant concentration.

When one or more NPMLs are involved in the plasmonic structures 50 or 50' then they should be one on top of the other and both of them can be porous with different porosities or one is porous and the other is a dense metal film. Their thicknesses will be determined according to the wavelength in use, the thicknesses of the top or under dielectric layers and the prism refractive index so that the contrast of the SPR dip is a maximum.

A thin nano-dimensional over-layer (for example 10 nm of Si for the visible range and few tens of nm of Si for the near infrared range or higher thicknesses even in the visible range if the refractive index is close to that of the analyte but in all cases the optical thickness should be less than the cutoff for guided modes to be generated in the top dielectric layer), on top of a silver layer was found by the inventor [7,8] to enhance the sensitivity in the angular interrogation by a factor of 3. Since the top layer thickness is less than the cutoff for exciting guided modes, this mode of operation was called nearly guided wave SPR (NGWSPR). Later it was found [9,10] that, when operated in the spectral interrogation mode, the SPR dip of NGWSPR sensors with top nano-dimensional high index layers becomes narrower than the case without the top layer by at least factor of 3 and their sensitivity increases and therefore the figure of merit (FOM) is improved (FOM is defined as the sensitivity divided by the width of the SPR dip). The present invention shows that using a Nano-Porous Metal Layer (NPML) with porosity in the range 5%-35% even further improves the FOM when a high refractive index layer is deposited on top of the metal. The diameter of the pores is measured in the nanoscale and is less than 100 nm. The design of such porous metal films is done using effective medium homogenization algorithms such as Maxwell-Garnett or the Brugemman formalisms and the use of the 4×4 matrix calculation approach developed by the inventor [17]. The nano-porous film is preferably prepared by the glancing angle deposition technique or alternatively it can also be prepared in a periodic manner using lithographic techniques.

Figures 4A, 4B:
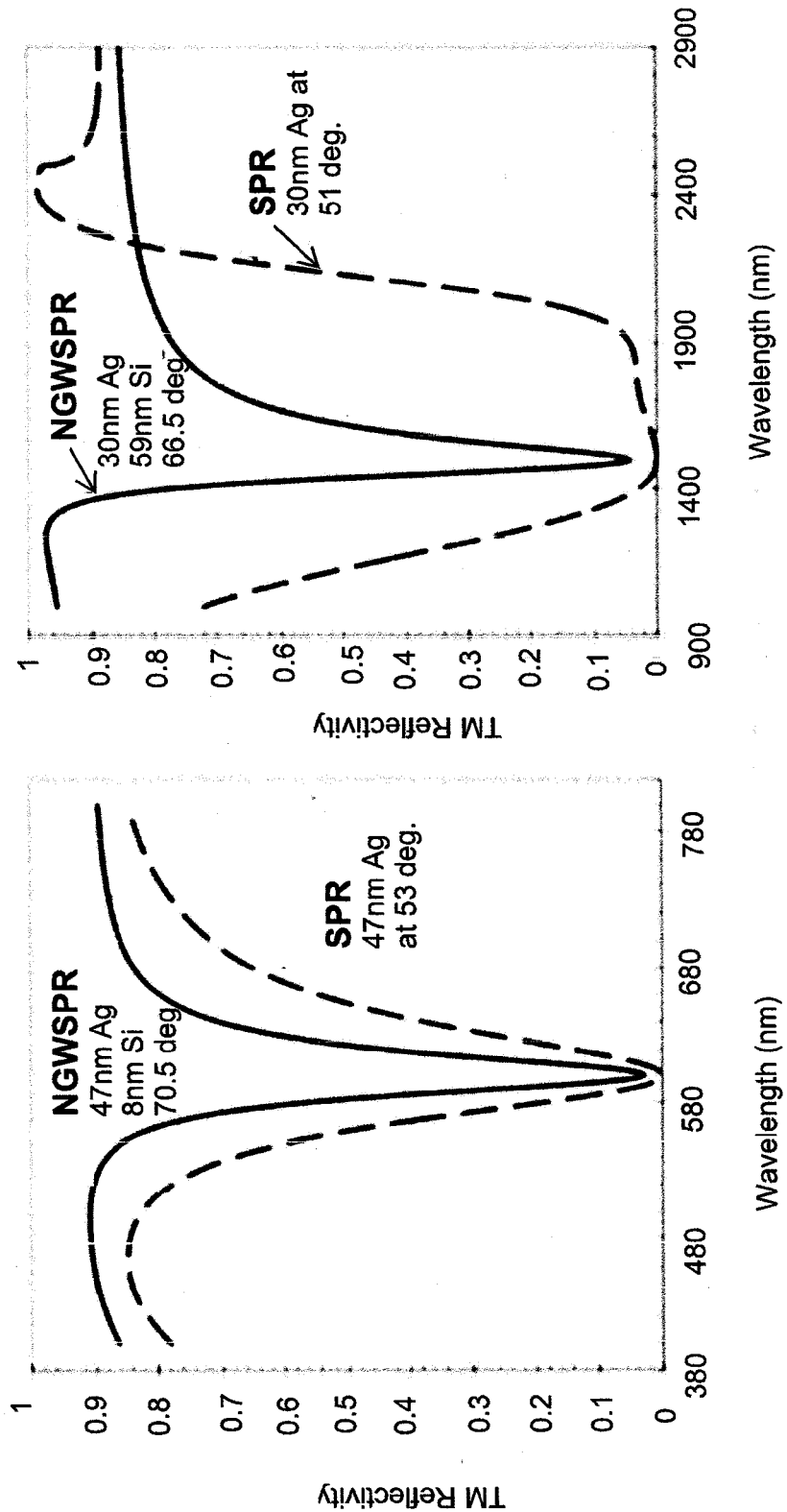
FIG. 4a and FIG. 4b show the calculated TM reflectivity in the KR configuration with and without a top nano-dimensional layer made of Si on top of porous metal layer in the visible range and in the infrared range respectively.

FIG. 4A and FIG. 4B show the calculated TM reflectivity in the KR configuration with (NGWSPR) and without (SPR) a top nano-dimensional layer made of Si on top of a porous metal layer in the visible range (FIG. 4a) and in the infrared range (FIG. 4b). The analyte is water with refractive index 1.33. The prism is SF11 and the other parameters are shown on the figure. From these figures it is clear that with the over-layer the dip becomes much narrower.

FIG. 5a shows the calculated spectral sensitivity and FIG. 5b shows the calculated figure of merit (FOM) as a function of the incidence angle for both SPR and NGWSPR structures. For the calculations a SF11 (Schott glass) prism was used, the analyte was RI ($n_a$=1.33), the porous Ag layer thickness was optimized to give full SPR matching condition, and the Si layer thickness was 10 nm. For the same range of incidence angles, the resonance wavelength varies from 530 nm to 860 nm in the SPR case, and from 820 nm to 1400 nm in the NGWSPR case. As shown in FIG. 5a the sensitivity is improved using NGWSPR, hence the end result is an improvement in the figure of merit (defined as sensitivity divided by the full width at half maximum of the SPR dip) as can be seen in FIG. 5b. It is one of the purposes of this invention to disclose a plasmonic substrate with superior sensitivity and advantages which combines all the separate structures listed above into one optimum structure.

Another embodiment of the substrate uses the long range SPR (LRSPR) configuration in combination with a nano porous metallic layer and a high index dielectric top layer. This embodiment requires a buried dielectric layer underneath the metal layer having an index approximately equals to that of the analyte (FIG. 3d). For example if the analyte is water then a Teflon© dielectric layer is usually used. However in the present invention a porous $SiO_2$ layer prepared by the glancing angle deposition (GLAD) technique with nearly 25% porosity is used. The refractive index of such a porous layer has been calculated and found to be close to that of water. Hence using the GLAD technique the buried layer, the porous metal layer and the top nano-dimensional layer can be prepared in one deposition chamber without the need for taking the substrate outside the chamber between depositions of the different layers. Since the high index top layer (made from Si 10 nm thick or thicker) also functions as a protection layer for the silver porous metal layer, using this methodology the sensor substrate obtained is stable against environmental effects such as oxidation. The thickness and refractive index of the top dielectric layer are optimized using the rigorous 4×4 transfer matrix approach for best sensitivity and penetration depth. For example with a buried dielectric layer of refractive index different from that of the analyte, the top dielectric layer may be chosen to have a refractive index close to that of the buried dielectric layer if larger penetration depth is required. Although in most cases of interest a refractive index higher than 2 and thickness of up to few tens of nm are adequate, the words nano-dimensional and high refractive index should not limit the invention to these values. In all cases the optical thickness of the top dielectric layer is less than the cutoff required to excite guided modes within the layer.

Figure 6:
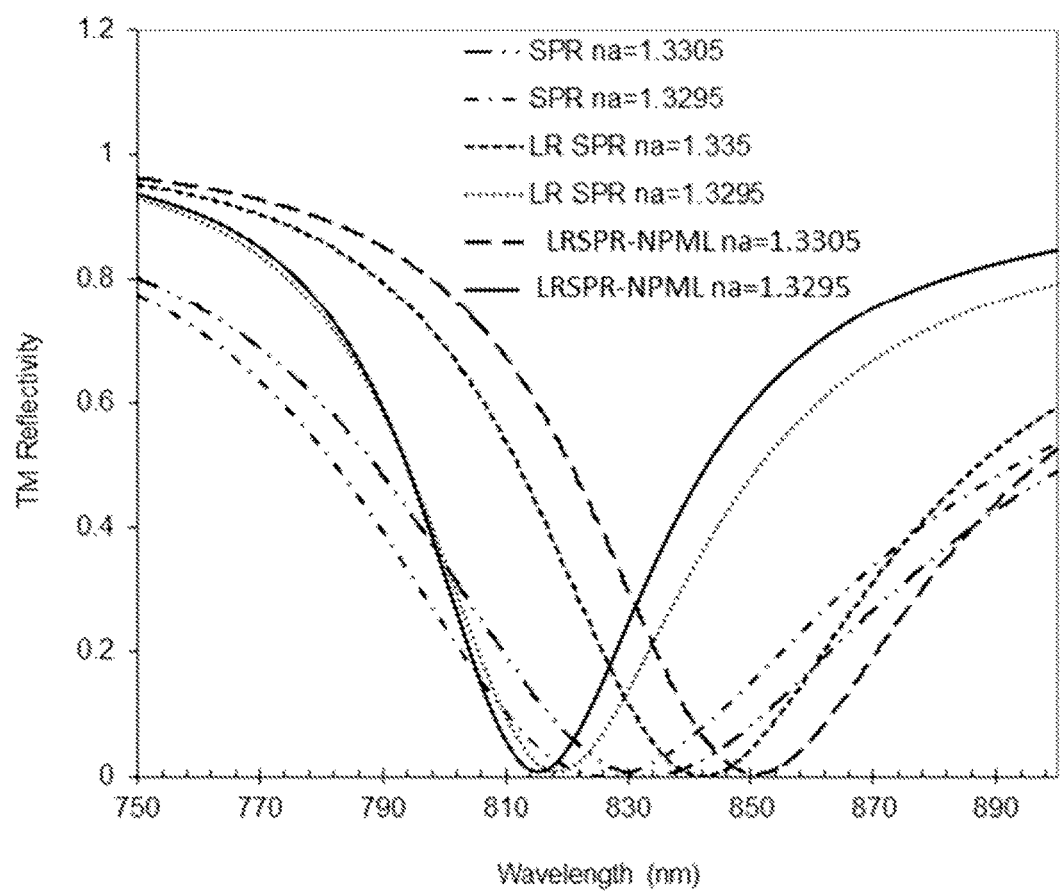
FIG. 6 shows calculated spectra at different analyte indices for three structures: SPR, LRSPR and LRSPR-NPML.

FIG. 6 shows calculated spectra at different analyte indices as indicated in the legend for three structures: SPR, LRSPR and LRSPR-NPML. The prism is BK7 glass. For the SPR case the metal is 50 nm gold, for the LRSPR case an additional 1188 nm teflon layer was used as the buried layer, and for the LRSPR case the same teflon layer was used but the metal layer is 30 nm gold with 30% porosity. The sensitivities obtained for the three cases are: 7250 nm/RIU, 23750 nm/RIU and 35500 nm/RIU respectively.

In FIG. 6 the SPR dip, which originates from the buried layer, is not shown. The sensitivity of the LRSPR-NPML is clearly superior over the other two cases. The reason for this superiority is the enhancement in the electromagnetic field distribution in the analyte, which becomes enhanced and spread over longer depth inside the analyte as can be easily seen in FIG. 7. The fact that the LRSPR-NPML gives higher sensitivity and larger penetration depth can be used for sensing large bioentities such as bacteria in water.

Figure 7:
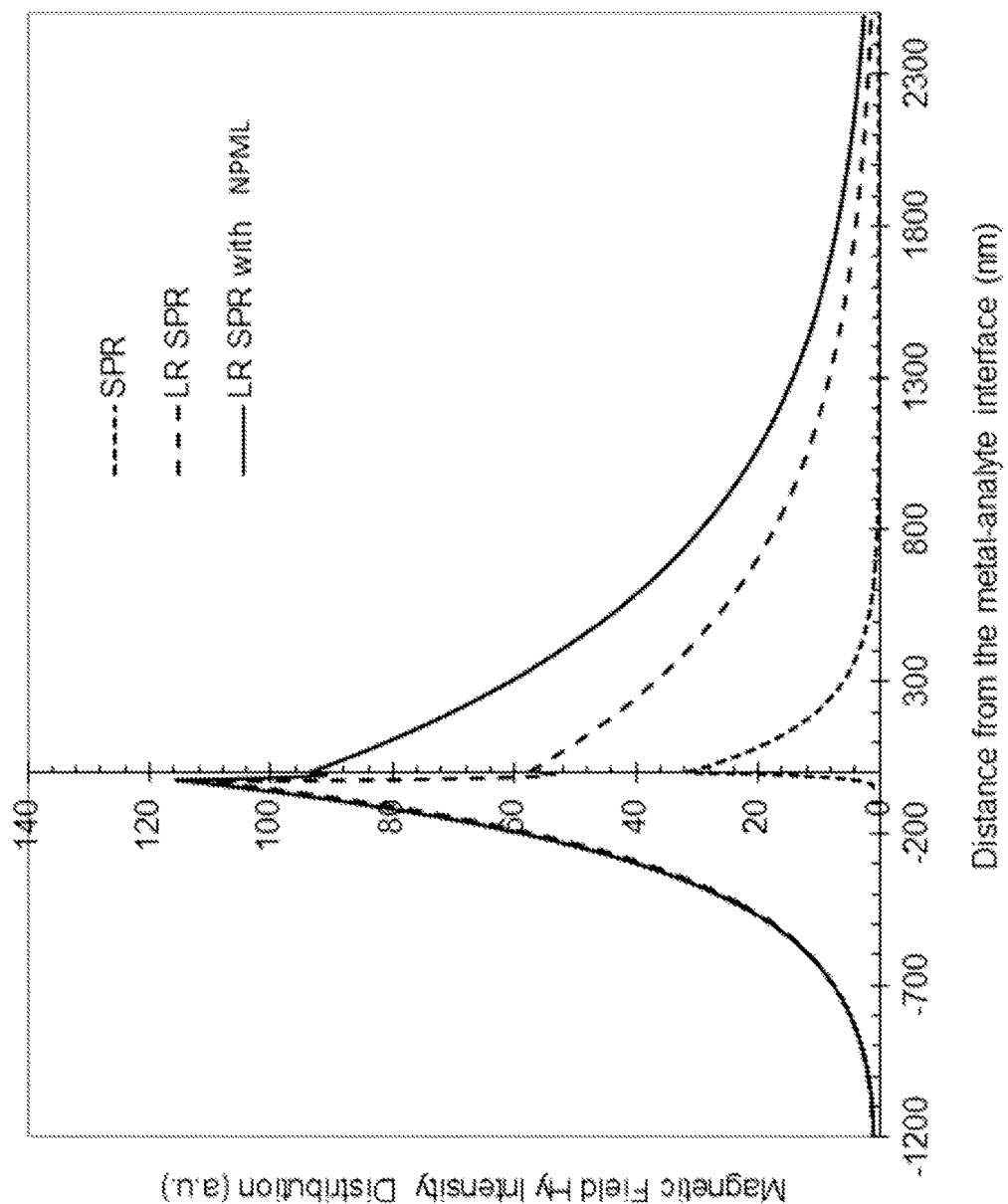
FIG. 7 shows calculated electromagnetic field distribution for three structures: SPR, LRSPR and LRSPR-NPML.

FIG. 7 shows calculated electromagnetic field distribution for three structures: SPR, LRSPR and LRSPR-NPML. The prism is BK7 glass and the wavelength used is 830 nm. Other parameters are the same as in FIG. 6. To obtain complete SPR matching the incidence angle was varied: 66.11 degrees for the SPR case, 62.02 degrees for the LRSPR case and 62 degrees for the LRSPR-NPML case.

Figure 8A:
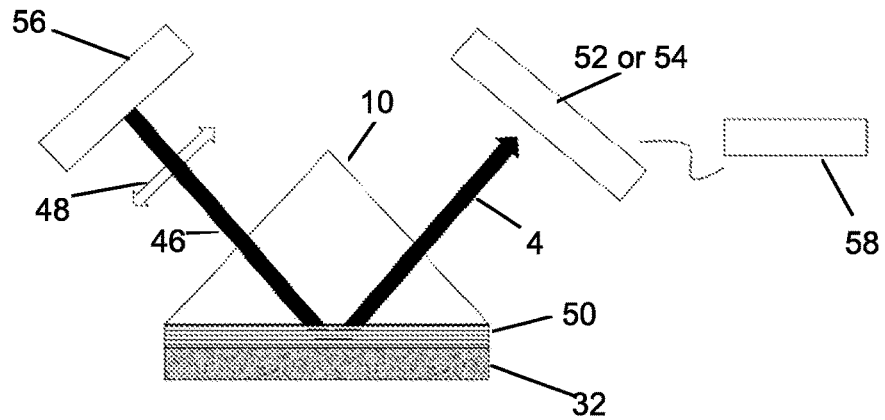
FIGS. 8a to 8c schematically show three optical arrangements that can be used to perform measurements according to different embodiments of the invention.
Figure 8B:
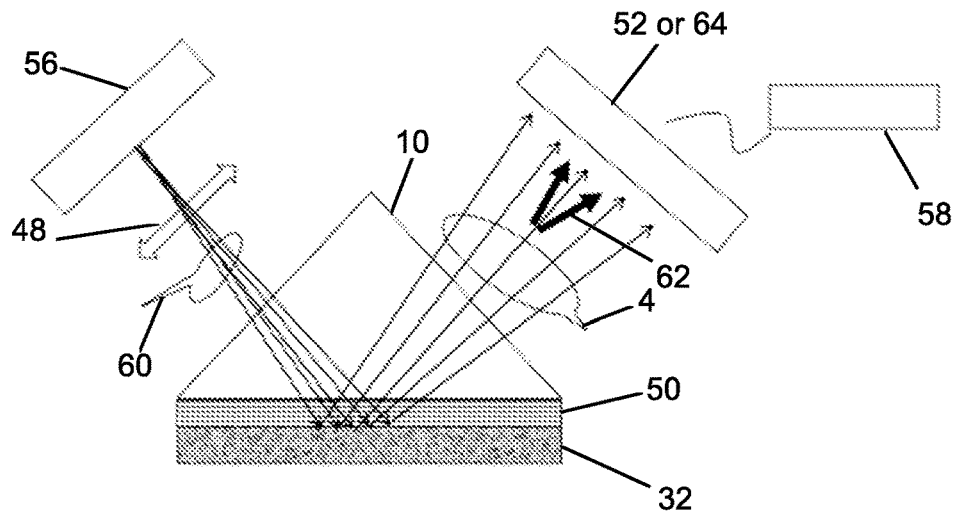
Figure 8C:
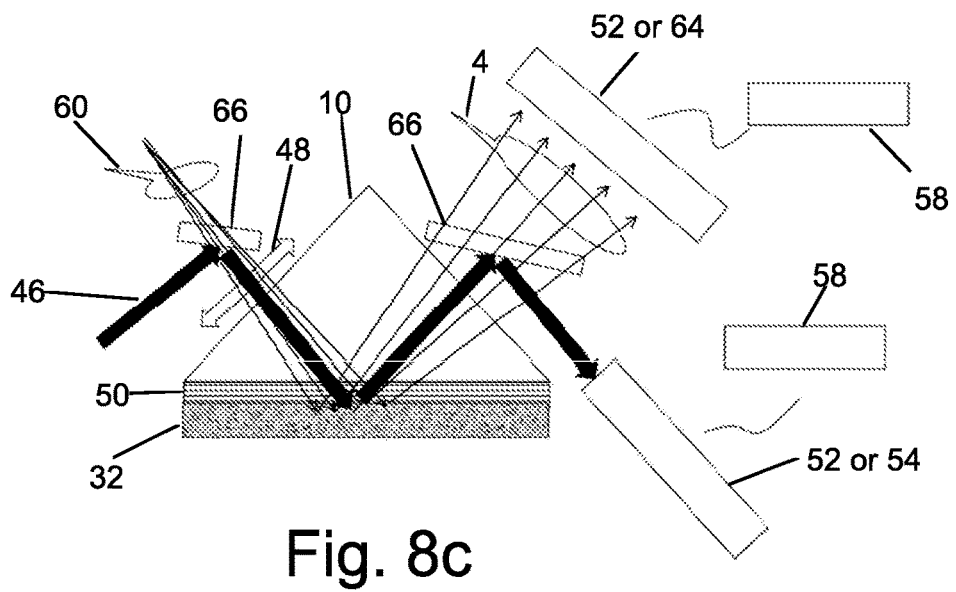

Spectral Versus Angular Interrogation Modes:

FIGS. 8a-8c schematically show three optical arrangements that can be used to perform measurements according to different embodiments of the invention.

FIG. 8a shows a schematic setup with which spectral or angular interrogations can be implemented. In this setup a collimated beam 46 passes through a polarizer 48 oriented along the TM direction, incident on the prism 10 and reflected from the multilayered structure 50 on top or the analyte 32 towards a detector or an array of detectors (one or more detectors are identified by numeral 52 in the figures) or a spectrometer 54. The output from detector 52 or spectrometer 54 is sent to a processor and display unit 58. In an embodiment input light from light source 56 is introduced via an optical fiber and the reflected output light 4 is collected and coupled to an optical fiber connected to a spectrometer 546. In the spectral mode the beam direction is fixed at a certain angle and the spectrum is grabbed with the spectrometer 54. In the LRSPR-NPML case two dips at different wavelengths are observed and the one that corresponds to the SP wave excited at the buried-layer-metal interface is used as a reference. The present invention enables the use of the color distribution of the reflected beam using a color camera or simply the naked eye by looking at a screen to decide on the presence of an analyte and to quantify it by comparison with the color distribution from a reference channel containing reference analyte.

Alternatively a tunable source is used or a tunable filter and a single pixel detector. In the angular mode the incidence angle can be scanned, however this option is slow and requires mechanically moving parts and therefore is not preferable.

FIG. 8b shows a setup in which a diverging beam 60 having a single wavelength is used and a detector array 52 or camera 64 measures the angular distribution of the intensity of the reflected beam 4. The dips appear as dark lines near the center of the field of view of the detector array or camera (the location is in the angular range shown symbolically as dark arrows 62) on a bright background. In the LRSPR-NPML case two dips appear where one of them corresponds to the SPR excited at the buried layer-metal interface and will be used as a reference. If a NPML is used without a buried layer then the reference dip will be obtained due to the Plasmon wave excited at the reference regions shown in FIG. 2.

One of the embodiments of this invention is the combination between the spectral and angular modes of the SPR sensor in one single and compact setup as shown in FIG. 8c. This embodiment be highly preferable for example when the spectral SPR is used in the infrared where detector arrays and cameras are costly. Therefore a spectral mode is used with a relatively less expensive spectrometer and, in parallel, the diverging beam approach is used with shorter wavelengths where cameras and detector arrays are not expensive. This combination is desirable when two analytes are needed to be detected simultaneously. For example the diverging beam at visible wavelengths can detect analytes within a range of 200 nm from the sensor surface while the infrared, which penetrates deeper, can detect analytes with large sizes or analytes that exist at larger distance from the sensor surface. In addition the diverging beam SPR can be used for monitoring the temperature of the sensor surface by monitoring the SPR dark line corresponding to a layer on top of the sensor surface with known refractive index and known thermo-optic coefficient. This embodiment is also important for easier alignment of the spectral SPR setup as the observation of the dark line on bright background is easier and its location tells about the angle of the SPR.

In FIG. 8c an incident quasi-monochromatic diverging beam 60 passes through a first dichroic mirror 66, polarizer 48 and prism 10 is reflected from the multilayered sensing element 50 and analyte 32 back through prism 10 and a second dichroic mirror 66 to either a detector array 52 or camera 64 and the detected signals are sent to a processor and display unit 58. The multilayered sensing element 50 of the invention is a plasmonic structure comprised of a Nano-structured Porous Metal Layer (NPML) and at least one of: (a) buried dielectric layer under the nano-porous metal layer; (b) a nano-dimensional high index layer on top of the metal layer; and (c) a molecular layer for bio-functionalization adjacent to an analyte layer. Simultaneously an incident wideband collimated beam 46 is reflected from the first dichroic mirror 66, passes through polarizer 48 and prism 10 is reflected from the multilayered sensing element 50 and analyte 32 back through prism 10 and is reflected by the second dichroic mirror 66 to either a detector array 52 or a spectrometer 54 and the detected signals are sent to a processor and display unit 58.

One Dimensional Diverging Beams and Means for their Generation:

The circularly diverging beam in FIG. 8b and FIG. 8c has the limitation that the plane of incidence is not well defined as rays exist within a cone of a certain angular aperture and not all the rays are TM polarized and as a result the contrast of the observed dips is low. This problem becomes severe with the mode of phase retardation measurement.

In this invention the use of a diverging beam mostly in the plane of incidence and having very little divergence in the orthogonal plane is disclosed with the options of controlling the divergence using a lens, a rectangular slit or a combination of both lens and rectangular slit. A beam generated in this manner is called a 1-D diverging beam. FIGS. 9a-9c are illustrations that clarify this issue further.

In FIG. 9a a beam originating from a point source S is drawn and the tips of some of the rays in the plane P are shown. All the rays represented by the dashed lines form a one dimensionally diverging beam because the beam only diverges in the xz plane (incidence plane) making an angle $\theta$ with the z-axis. The projections of all these rays in the xz plane (dashed rays) are all parallel to the z-axis. On the other hand the ray represented by the solid line is not in the xz plane and its projection in the yz plane makes an azimuth angle $\phi$ with the z-axis because it is slightly diverging also along the y-axis. Hence when this beam is incident on a flat interface, all the rays represented by the dashed lines have a common plane of incidence (xz) while the ray represented by the solid line has a different plane of incidence. Therefore if the rays represented by the dashed lines are polarized in the plane of the incidence (TM polarization) the ray represented by the solid line will have a TE polarization component. Since one of the necessary conditions for exciting SP wave is for the wave to be TM polarized, the ray represented by the solid line cannot excite an SP wave completely. As a result the contrast of the SPR will be reduced. In addition, because the polarization of some of the rays is not pure TM, it is difficult to perform phase imaging.

FIG. 9b illustrates a pure 1-D diverging beam generated from a line source. All the rays diverge only in the xz plane and so for the cross section of the beam with wave vector component along x that satisfies the SPR excitation condition $k_x=k_{sp}$ (represented by equation 1 for prism coupling); a dark line on bright background with high contrast will appear in the reflected beam.

Examples of methods to generate the 1-D diverging beam are:

a. Laser diodes (LDs) are by their nature diverging in the propagation direction much more than the orthogonal direction. This property of LDs is called astigmatism. Hence the use of LDs with high astigmatism is expected to give SPR images with high contrast. The use of standard LD and photodetectors array was proposed in [18] with a standard plasmonic substrate (dense film) and one polarizer at the input. However usually standard low cost LDs have a non-uniform beam and due to the speckle noise associated with laser beams this option as described in [18] is not the most preferable. As part of the present invention the following methods to overcome this problem by performing spatial filtering and controlling the divergence have been developed:

(i) a lens (or a two lens system) is used to focus the LD beam into a slit with its long axis along the long beam axis, small enough in the perpendicular direction to perform spatial filtering of the beam, and yet without changing the beam divergence. For controlling the beam divergence an additional positive lens is used after the slit. According to the thin lens law 1/U+1/V=1/F, where U and V are the object and image distances from the lens and F the focal length. When the slit is in the back focal plane (U=F) of the $2^{nd}$ lens, the beam will be collimated (V→∞), but when it is out of the focal plane (U<F) the beam will be diverging (V<0) and the amount of divergence is controlled by changing the deviation from the focal plane. For further divergence of the beam, a negative lens may be added;

(ii) A second configuration is to use the spatial filtering properties of single mode fibers. Hence coupling the LD to a single mode fiber will give a clean and uniform beam, however it will be circular. To make it rectangular, a slit may be used to stop the majority of the rays not propagating in the plane of incidence, as shown in FIG. 9c. The fiber itself can have a rectangular end, or alternatively a one dimensional array of single mode fibers is used.

b. Another way to generate a 1-D diverging beam is the use of a light emitting diode (LED) with narrow enough bandwidth in order not to widen the angular resonance, or a non-coherent source and a cylindrical lens to generate a line at its focal plane from a collimated beam. A collimated beam will be focused to a line using a cylindrical lens. After the focus this line will then become diverging in one direction thus forming a 1-D diverging beam. In [19] the inventor claimed the use of a cylindrical lens to generate a one dimensionally diverging beam combined with a standard plasmonic substrate and using one polarizer at the input.

c. Another embodiment is the use of a rectangular slit as a spatial filter in the diverging beam path of any diverging beam (from LD, LED, lamp, etc.) in order to block all the beams that are not diverging in the incidence plane. The size of the slit and its position with respect to the source determines the divergence angle. In FIG. 9c, a scheme is shown in which a one dimensionally diverging beam is generated from a circular beam using a slit. The rays passing through the slit aperture are mainly the ones near the xz plane (incidence plane).

d. Other ways of generating a 1-D diverging beam include the methods described in a-c above to convert the following sources of collimated beams into 1D diverging beams: The collimated beam can be generated from a point source at the back focal plane of a circular lens. A collimated beam can be obtained from a collimated laser and using a beam expander to expand its radius. A point source could be a laser diode or a pinhole of up to few tens of microns diameter. A point source could also be the output end of a single mode fiber.

Figure 10:
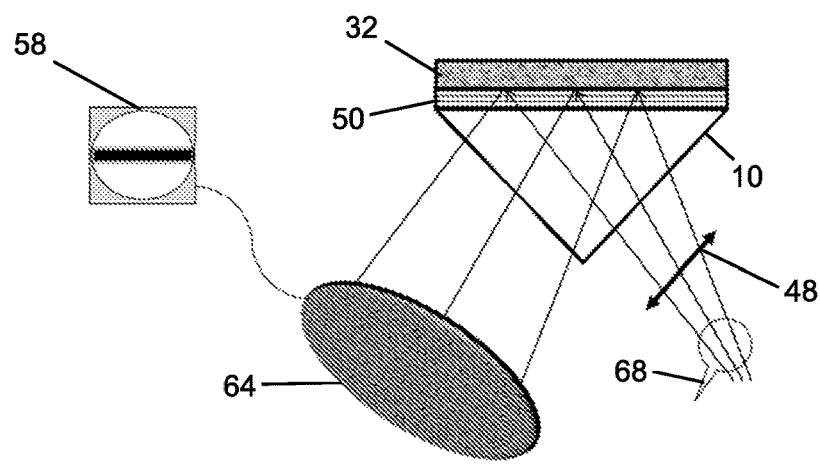
FIG. 10 schematically shows an embodiment of a sensing scheme in which a TM polarized 1D diverging quasi-monochromatic beam is incident on the prism with a SPR substrate attached to it and is reflected towards a camera.

Examples of Sensing Configurations Using the Plasmonic Structure of the Invention:

FIG. 10 schematically shows a sensing scheme in which a 1D diverging quasi quasi-monochromatic beam 68 is polarized using a linear polarizer 48 so that all rays constituting the beam have the same incidence plane and are polarized in the plane of incidence (TM). The beam is incident on a prism 10 with a SPR structure 50 of the invention created either directly on a face of the prism or on a substrate (not shown in the figure) that is attached to the prism and analyte 32 attached to structure 50 using an index matching fluid and is reflected towards a camera 64. The camera image displayed on the monitor 58 is a dark line on a bright background if a single channel is used (uniform substrates) or many dark lines shifted with respect to each other if many channels are used. With the LRSPR-NPML configuration two lines will be observed for the two plasmons generated at the two surfaces of the metal film, where one of the lines will not be sensitive to the analyte refractive index and so can be used as a reference. The position of the dark line is a function of the refractive index of the analyte and hence a function of the concentration of pollutants. The angular size of the beam is chosen so that it covers at least the whole angular range of the SPR excitation from all channels and its size is within the active area of the camera. Since the beam is diverging then its size depends on the propagation distance. In order to avoid situations where the camera has to be placed too close to the prism, a converging lens can be placed in front of the camera in order to bring the size of the diverging beam to within the camera's active area.

Figure 11A:
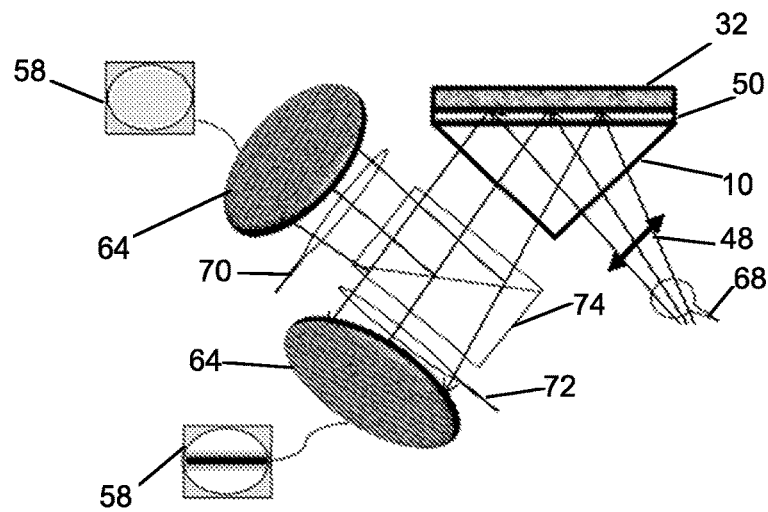
FIG. 11a and FIG. 11b schematically show embodiments of a sensing scheme in which a 1D diverging quasi-monochromatic beam, which is polarized half TM and half TE is incident on the prism with an attached SPR substrate.
Figure 11B:
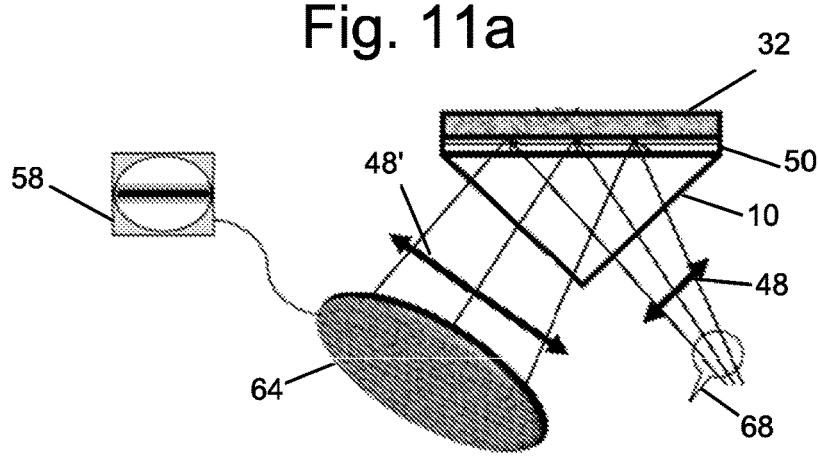

FIG. 11a and FIG. 11b schematically show embodiments of a sensing schemes in which an input polarizer 48 is oriented at 45 degrees so that two equally polarized components of a 1D diverging quasi-monochromatic beam 68 are generated—a TE component 70 and a TM component 72. When the beam is reflected at the SPR structure 50 the TM part undergoes a large phase change while the TE does not. As a result phase retardation is produced between the two components. In FIG. 11a a polarized beam splitter 74 is introduced which directs each of the polarization components TE and TM to different cameras 64 and processors and displays 58. The two images grabbed may then be subtracted and normalized to give the Stokes parameter S1. Alternatively the two signals are divided one by the other to generate a normalized SPR image because the TE polarized part is totally reflected and thus has the same shape as the incident beam. This latter normalized image is in fact equivalent to the ellipsometric parameter image: tan (ψ) defined below. Alternatively the phase of one of the beams is modified with respect to the other using a passive or active element to allow obtaining the ellipsometric parameters.

In FIG. 11b another scheme is depicted in which an output linear polarizer 48' situated before the camera 64 analyzes the beam so that the output signal depends on the phase retardation and the analyzer 48' orientation with respect to the first polarizer 64. In order to find a methodology to measure the ellipsometric parameters the inventor suggests a three point algorithm based on three orientations of the analyzer. The Jones vector after the polarizer is given by:

$$E_{input} = \frac{E_0}{\sqrt{2}} \begin{pmatrix} 1 \\ 1 \end{pmatrix} \tag{4}$$

Assuming the analyzer is oriented at an angle A with respect to the TM orientation, its Jones matrix is given by:

$$\hat{A} = \begin{pmatrix} \cos^2 A & \sin A \cos A \\ \sin A \cos A & \sin^2 A \end{pmatrix} \tag{5}$$

The reflection matrix of the sample is given by:

$$\hat{S} = \begin{pmatrix} \tan\psi \exp(i\Delta) & 0 \\ 0 & 1 \end{pmatrix} \tag{6}$$

The Jones matrix for the sample and polarizer is:

$$\hat{A}\hat{S} = \begin{pmatrix} \cos^2 A \tan\psi \exp(i\Delta) & 0.5 \sin 2A \\ 0.5 \sin 2A \tan\psi \exp(i\Delta) & \sin^2 A \end{pmatrix} \quad (7)$$

The signal on the camera is then given by:

$$I = I_0 \lfloor 0.5 + 0.5 \tan^2\psi + 0.5(\tan^2\psi - 1)\cos 2A + \tan\psi \cos \Delta \sin 2A \rfloor \quad (8)$$

where $I_0$ represents the signal coming from the source and other reflections of the optical system. The angle $$\psi = \arctan\left|\frac{E_{TM}}{E_{TE}}\right|,$$

together with the retardation $\Delta$, define the polarization state arriving at the detector, where $E_{TM}$ and $E_{TE}$ and $E_{TE}$ represent the complex amplitudes for the light polarizations along TM and TE respectively arriving at the detector. In order to determine $\psi$ and $\Delta$, at least three measurements must be made, for example by choosing three different polarizer-analyzer orientations. A suitable configuration is obtained when the analyzer is oriented at the three different orientations: $A=-\pi/4$, $0$, $\pi/4$. The signals then obtained are:

$$I_{ps} = I\left(A = -\frac{\pi}{4}\right) = 0.5 I_0 \{1 + \tan^2\psi - 2\tan\psi\cos\Delta\} \quad (9)$$

$$I_{45} = I(A = 0) = I_0 \tan^2\psi \quad (10)$$

$$I_{pp} = I\left(A = \frac{\pi}{4}\right) = 0.5 I_0 \{1 + \tan^2\psi + 2\tan\psi\cos\Delta\} \quad (11)$$

These equations can be solved to yield the following expressions for $\psi$, and $\Delta$:

$$\tan\psi = \sqrt{\frac{I_{45}}{I_{pp} + I_{ps} - I_{45}}} \quad (12)$$

$$\cos\Delta = \frac{1}{2\tan\psi} \frac{I_{pp} - I_{ps}}{(I_{pp} + I_{ps} - I_{45})} \quad (13)$$

The angles $\Delta$ and $\psi$ as a function of the wavelength contain the necessary information about the anisotropy, the refractive indices dispersions and the layer thicknesses. Note that in equations (12) and (13) ratios between the different intensities appear, hence the insensitivity to the source intensity fluctuations. In this way a more accurate measurement and better limit of detection are obtained.

The polarization angles can be controlled mechanically or preferably electronically using two liquid crystal retarders with their axis oriented at 45 degrees with respect to each other (see for example the rotator described by the inventor in [20]). This is the essence of the embodiment described in FIG. 12a. Since with SPR experiments the TE reflectivity is almost 100% then tan $\psi$ represents the same shape as the TM reflectivity. Hence with this methodology both the intensity and the phase information are obtained very precisely.

Figure 12A:
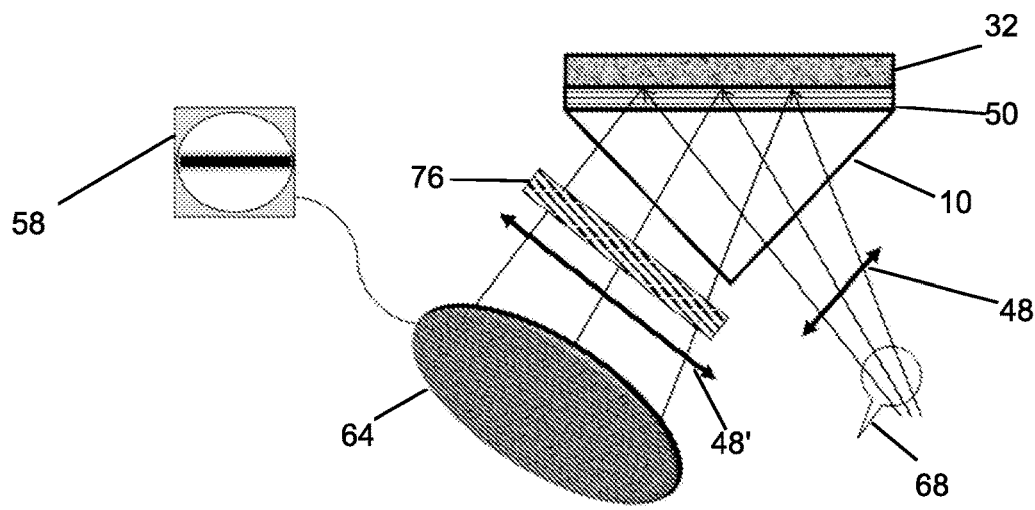
FIG. 12a schematically shows an embodiment of a sensing scheme in which a 1D diverging quasi-monochromatic beam, which is polarized half TM and half TE is incident on the prism with an attached SPR substrate and is reflected passing through a polarization rotator or phase modulator and fixed linear polarizer on its way to a camera.

FIG. 12a shows a setup in which a 1D diverging quasi-monochromatic beam 68 passes through an input linear polarizer 48 oriented at 45 degrees to the TM component and prism 10 and is reflected from multilayered sensing element 50 on top of analyte 32. The reflected wave passes through a polarization rotator or phase modulator 76 and an output linear polarizer 48' and falls on camera 64. Signals representing the camera image are sent to processor and display unit 58.

Using a similar analysis to the case of a rotating analyzer, for the case of a polarization rotator at an angle $\rho$:

$$I = I_0 \lfloor 0.5 + 0.5 \tan^2\psi + 0.5(\tan^2\psi - 1)\cos 2(A+\rho) + \tan\psi \cos\Delta \sin 2(A+\rho) \rfloor \quad (14)$$

Hence by fixing A=0 degrees, an expression analogous to equation (8) is obtained with the angle A replaced by the rotation angle $\rho$ of the rotator hence if the following orientations are chosen: $\rho = -\pi/4$, $0$, $\pi/4$:

$$I_{\rho-45} = I\left(\rho = -\frac{\pi}{4}\right) = 0.5 I_0 \{1 + \tan^2\psi - 2\tan\psi\cos\Delta\} \quad (15)$$

$$I_{\rho 0} = I(\rho = 0) = I_0 \tan^2\psi \quad (16)$$

$$I_{\rho 45} = I\left(\rho = \frac{\pi}{4}\right) = 0.5 I_0 \{1 + \tan^2\psi + 2\tan\psi\cos\Delta\} \quad (17)$$

These equations can be solved to yield the following expressions for $\psi$, and $\Delta$:

$$\tan\psi = \sqrt{\frac{I_{\rho 0}}{I_{\rho 45} + I_{\rho-45} - I_{\rho 0}}} \quad (18)$$

$$\cos\Delta = \frac{1}{2\tan\psi} \frac{I_{\rho 45} - I_{\rho-45}}{(I_{\rho 45} + I_{\rho-45} - I_{\rho 0})} \quad (19)$$

Other methods usually used for measuring the ellipsometric or the polarimetric parameters of the reflected light can be used here such as interferometric techniques or the use of a phase modulator instead of the polarization rotator. For example using a phase retarder with retardation $\Gamma$ of the polarization rotator the expression for I becomes:

$$I = I_0 \lfloor 0.5 + 0.5 \tan^2\psi + 0.5(\tan^2\psi - 1)\cos 2A + \tan\psi \cos(\Delta - \Gamma)\sin 2A \rfloor \quad (20)$$

Using three different phase retardations:

$\Gamma = 0 \Rightarrow I_{\Gamma 0} = I_0 \lfloor 0.5 + 0.5 \tan^2\psi + 0.5(\tan^2\psi - 1)\cos 2A + \tan\psi \cos\Delta \sin 2A \rfloor$ $\Gamma = \pi/2 \Rightarrow I_{90} = I_0 \lfloor 0.5 + 0.5 \tan^2\psi + 0.5(\tan^2\psi - 1)\cos 2A + \tan\psi \sin\Delta \sin 2A \rfloor$ $\Gamma = \pi \Rightarrow I_{180} = I_0 \lfloor 0.5 + 0.5 \tan^2\psi + 0.5(\tan^2\psi - 1)\cos 2A - \tan\psi \cos\Delta \sin 2A \rfloor$ Which are reduced further if A=−45 degrees.

$\Gamma = 0 \Rightarrow I_{\Gamma 0} = I_0 \lfloor 0.5 + 0.5 \tan^2\psi - \tan\psi \cos\Delta \rfloor \quad (21)$ $\Gamma = \pi/2 \Rightarrow I_{90} = I_0 \lfloor 0.5 + 0.5 \tan^2\psi - \tan\psi \sin\Delta \rfloor \quad (22)$ $\Gamma = \pi \Rightarrow I_{180} = I_0 \lfloor 0.5 + 0.5 \tan^2\psi + \tan\psi \cos\Delta \rfloor \quad (23)$ After some algebra the following equations are obtained:

$$\cos\Delta = \frac{I_{180} - I_{\Gamma 0}}{2\sqrt{0.25(I_{\Gamma 0} - I_{180})^2 + (I_{90} - 0.5(I_{\Gamma 0} + I_{180}))^2}} \quad (24)$$

$$\sin 2\psi = 2\frac{\sqrt{0.25(I_{\Gamma 0} - I_{180})^2 + (I_{90} - 0.5(I_{\Gamma 0} + I_{180}))^2}}{I_{\Gamma 0} + I_{180}} \quad (25)$$

In another embodiment it is also possible to rely on one of the signals described in equations (9-11) or (15-17) or (21-23) with an option to normalize to the incident wave intensity $I_0$. In particular the signal between crossed polarizers $I_{ps}$ is of interest to use for sensing as the crossed polarization reduces the effects of scatterings and reflections from the surfaces. In another embodiment the Stokes parameter can be used as the signal for sensing which is given by the difference signal: $S_1=I_{pp}-I_{ps}$ with an option for normalization to the incident beam distribution $I_0$.

Figure 12B:
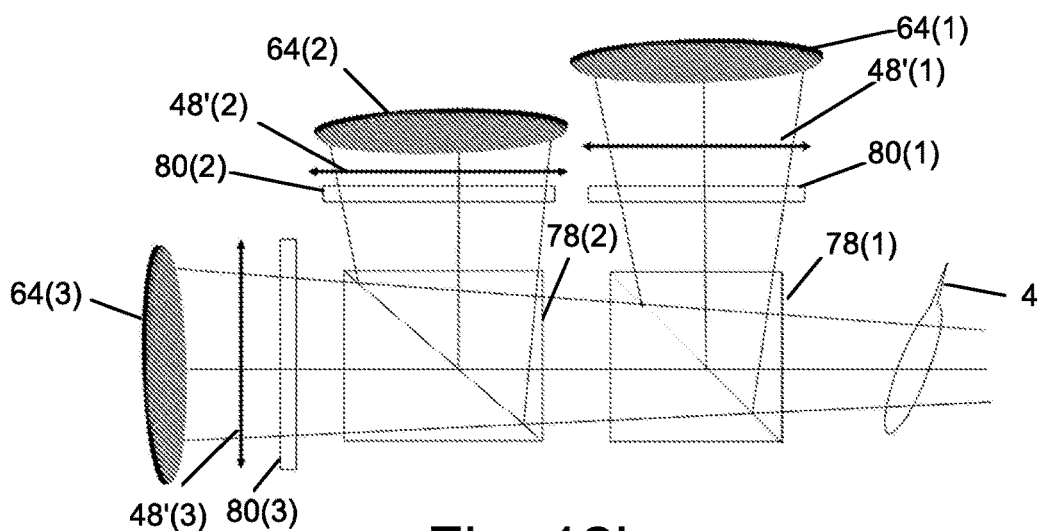
FIG. 12b schematically shows an embodiment of a sensing scheme which uses three cameras and passive polarizing elements in front of each camera to provide three analyzer orientations or three phase retardations combined with fixed analyzer.

In another embodiment sketched in FIG. 12*b* three analyzer states or three phase modulation values may be provided passively on three different equal parts of the output (reflected) beam. In this case the output beam 4 will be split into three equal beams using a combination of two nonpolarizing beam splitters 78(1) and 78(2). For example the first beam splitter 78(1) reflects 33.3% of the output towards camera 64(1), while 66.6% is transmitted, hits a 2nd beam splitter 78(2) with splitting ratio of 50/50 to generate two more images on cameras 64(2) and 64(3). The optical distances of the three cameras are such that the images sizes are the same in all the cameras. In case of three analyzers 48'(1), 48'(2), 48'(3) (no wave plates 80(1), 80(2), 80(3) are used in this embodiment) each one of the generated three images will then experience a different analyzer orientation $A=-\pi/4, 0, \pi/4$, and in case of phase modulation then three states are generated using the passive waveplates (80(1), 80(2), 80(3)) that give $\Gamma=0, \pi/2, \pi$, together with the same fixed analyzer orientation before each camera oriented at $A=-45$ degrees. The three waveplates are a full waveplate, a quarter waveplate and a half waveplate respectively. 80(1) can be a full waveplate or simply be a piece of glass with no birefringence of the same optical thickness as 80(1) and 90(2) plus the optical thickness difference generated by 78(2). The orientation of the optic axis of the waveplates is either along the TE or the TM polarizations of the diverging beam so that the required phase retardation is generated without changing the amplitudes of each polarization component. The three images obtained in each case are then processed according to equations (12, 13) for the case of three different analyzer orientations (no waveplates) or according to equations (24, 25) for the case of three different phase retardations generated with (80(1), 80(2), and 80(3)) and fixed analyzers at $A=-45$ degs.

In another embodiment a continuously rotating analyzer, rotator or continuously variable phase retarder can be used since in all of these three cases the signals from equations 8, 14 and 20 may be written as:

$$I=I_{dc}+I_s \sin \zeta + I_c \cos \zeta \quad (26)$$

Where $\zeta=2A, 2\rho, \Gamma$ in accordance to which technique is used. Hence grabbing the time dependent signal while $\zeta=2A, 2\rho, \Gamma$ is changing continuously and performing Fourier transform on the data the coefficients $I_{dc}, I_s, I_c$ are obtained from which the elliposmetric parameters can be determined. From the Fourier components $I_{dc}, I_s, I_c$ one can then determine the ellipsometric parameters. Alternatively one can use $I_{dc}, I_s, I_c$ components themselves or a combination of them to measure the analyte refractive index variations.

Another embodiment of the invention is when some imaging optical components are added to the light paths between the source and the different detectors so that an image of the interface of the analyte with the plasmonic multilayered structure is created on each detector. Particularly important is the phase image which will be extracted from images from two or three detectors so that transparent objects in the analyte interface such as cells can then be seen easily.

Figure 13:
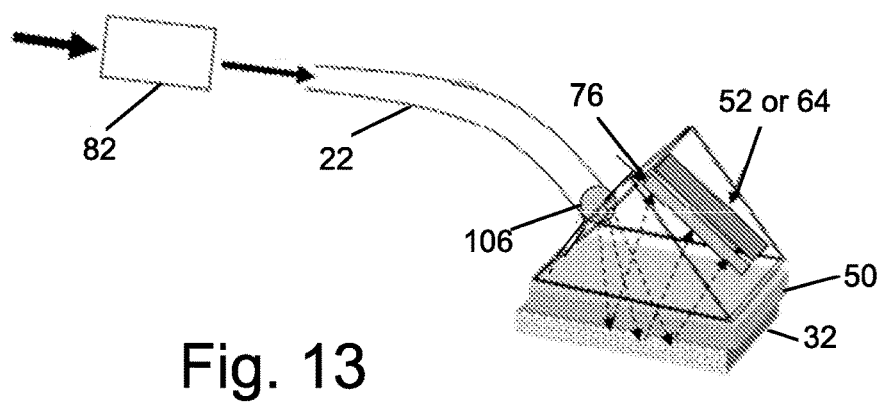
FIG. 13, schematically shows an embodiment of a compact sensing scheme.

Another embodiment, schematically shown in FIG. 13, comprises assembling the above setups into a compact unit connected to a cable in which an optical fiber 22 is enclosed. Broadband light passes through a tunable filter 82 to produce narrowband light that enters the optical fiber 22 to provide the light to the module while in a return sleeve electrical wires are enclosed for the detector array 52 or camera 64 and the polarization rotator 76. The output end of the optical fiber 106 is configured to give a 1-D diverging beam by one of the methods described herein above.

Figure 14:
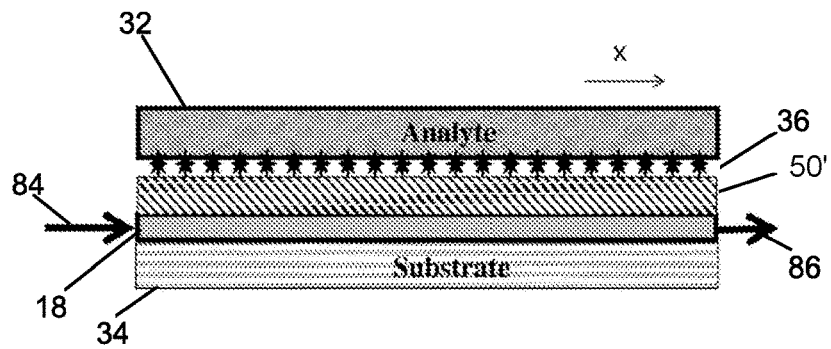
FIG. 14 schematically shows an embodiment of a sensing scheme which uses a waveguide coupling technique.

Another embodiment of a sensing scheme uses the waveguide coupling technique as shown in FIG. 14. The input light could be monochromatic and the angular profile at the output is then detected or it can be a wideband source and the output spectrum is then measured using spectral interrogation. For multichannel operation then each channel has its own light coupling and detection means.

In FIGS. 14, 15*a*, 15*b*, and 16 the elements shown are identified as follows: input light 84, output light 86, analyte layer 32, multilayer sensing element 50' (comprising a nanostructured porous metal layer and at least one of a buried dielectric layer and a nano-dimensional high index layer), functionalization layer 36, substrate 34, transparent substrate 88, waveguide layer 18, and optical fiber 22.

Figure 15A:
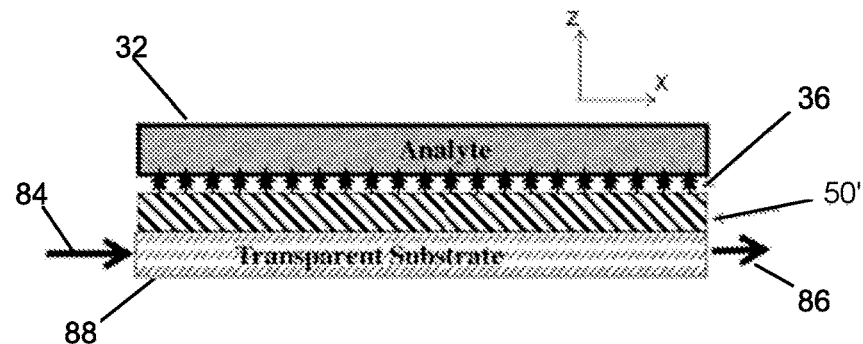
FIGS. 15a and 15b schematically show an embodiment of a sensing scheme that uses a transparent substrate as a light pipe.
Figure 15B:
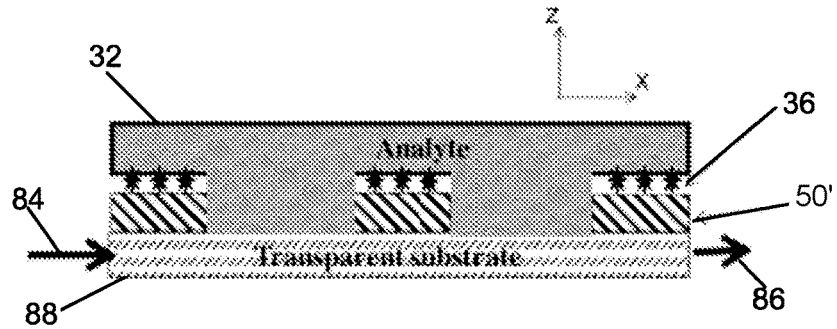

Another sensing scheme uses a transparent substrate as a light pipe as shown schematically in FIGS. 15*a* and 15*b* for single channel and multichannel embodiments respectively. The light pipe could be thin from few tens of microns up to 1-2 mm thickness. The multilayered SPR structure and the analyte can be on one face of the light pipe or in its two large faces. One option is to have the multilayered SPR structure on one face only while the opposite face is covered with a mirror. The input light could be monochromatic, in which case the angular profile at the output is detected with a camera, processed and correlated with refractive index changes of the analyte. Alternatively a wideband source is used and the output spectrum is then measured in the spectral interrogation using a spectrometer. The input light is preferably diverging in the xz plane and TM polarized in order to improve the contrast and hence the detection limit of the device. The 1-D diverging beam in the xz plane can be achieved using any of the means described hereinabove. For multichannel operation then all the channels can be in parallel and each channel has its own light coupling and detection means or more preferably the channels are arranged in series on the same substrate (FIG. 15*b*) but differentiated by a different over-layer having high refractive index over each channel. In the latter case the monitoring of the output beam is only through the spectral interrogation mode. The light pipe configurations in FIGS. 15*a* and 15*b* can operate in reflection mode in which a mirror is deposited on the output face and the reflected light is monitored with free space optics or using fiber optic Y-coupler connected at its output end to a spectrometer.

Figure 16:
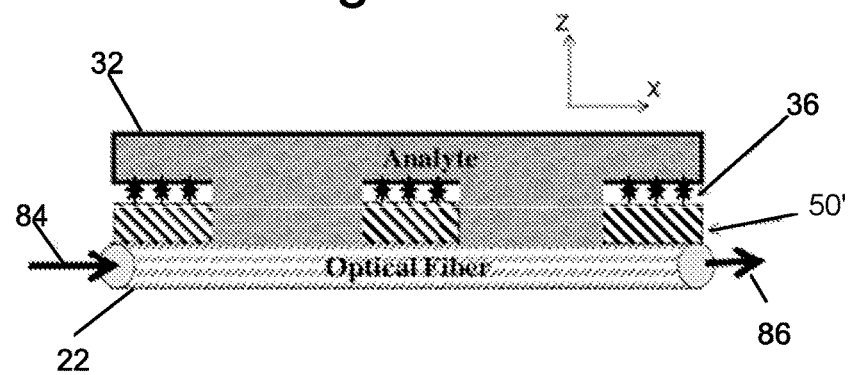
FIG. 16 schematically shows an embodiment of a sensing scheme that uses a part of an optical fiber core with the multilayered sensing element deposited directly on the exposed part of the fiber core.

Another embodiment of a sensing scheme uses an exposed area of a single mode optical fiber as shown in FIG. 16 with the multilayered sensing element deposited directly on the side of the fiber. One method to expose the core of the fiber is polishing the cladding in the area of interest. Alternatively plastic or polymer clad fibers can be used in which the clad can be easily removed mechanically or chemically. In this latter case the whole core circumference area may be used for sensing, thus improving the detection limit. A wideband source is used and the output spectrum is then measured in the spectral interrogation mode using a spectrometer. For multichannel operation (as shown in FIG. 16) all the channels are arranged in series on the same fiber but differentiated by different top nano-layers with high refractive index deposited on top of the metal layer.

Figure 17:
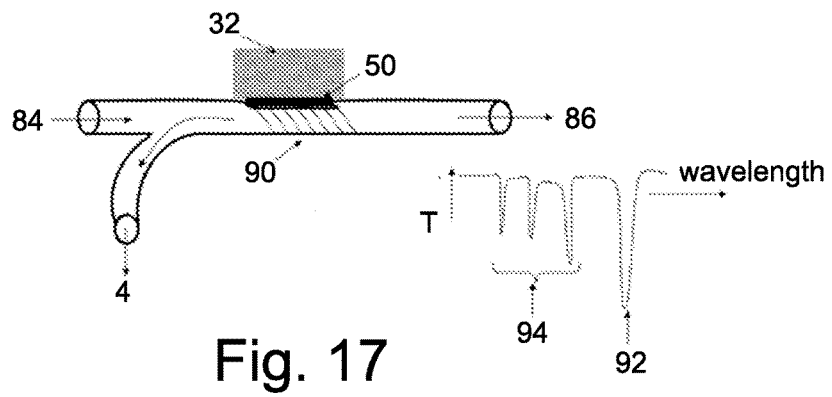
FIG. 17 schematically shows an embodiment of a sensing scheme that uses tilted fiber gratings as a means to couple light into the fiber cladding and thus excite SPR.

Another embodiment uses tilted fiber gratings (TFG) which can be written in the core of photosensitive fibers using the same technique as for standard fiber grating writing, except for the small modification of generating a small azimuthal angle of the writing pattern (mask or fringe pattern). The most important property of this embodiment is the fact that TFGs can couple light into the cladding. Hence they can excite surface Plasmon waves if a proper metallic film is deposited on top of the grating (see FIG. 1). Several papers [11,12,13,14,15] and a patent[16] have already been published on the subject showing the potential of this device for sensing. The present invention uses the novel multilayered structure disclosed herein above as the sensing element in combination with tilted fiber gratings. In FIG. 17, a single channel configuration is drawn both in reflection and transmission modes. Multichannel operation is also disclosed here in a similar manner to the serial arrangement shown in FIG. 16 with the top high index layer differentiating between the different channels.

In the setup shown in FIG. 17 the input light 84 is either broadband or from a tunable light source. The light travels in optical fiber 22 until it encounters a TFG 90 where part of the light is reflected 4 and part is transmitted 86. Over the TFG a multilayered sensor element 50 of the invention is created and covered by the analyte layer 32. In the lower left side of FIG. 17 is shown a graph of wavelength vs. intensity of the transmitted light. This graph shows the large absorption peak 92 of the core mode and the smaller absorption peaks 94 of the cladding modes.

Figure 18:
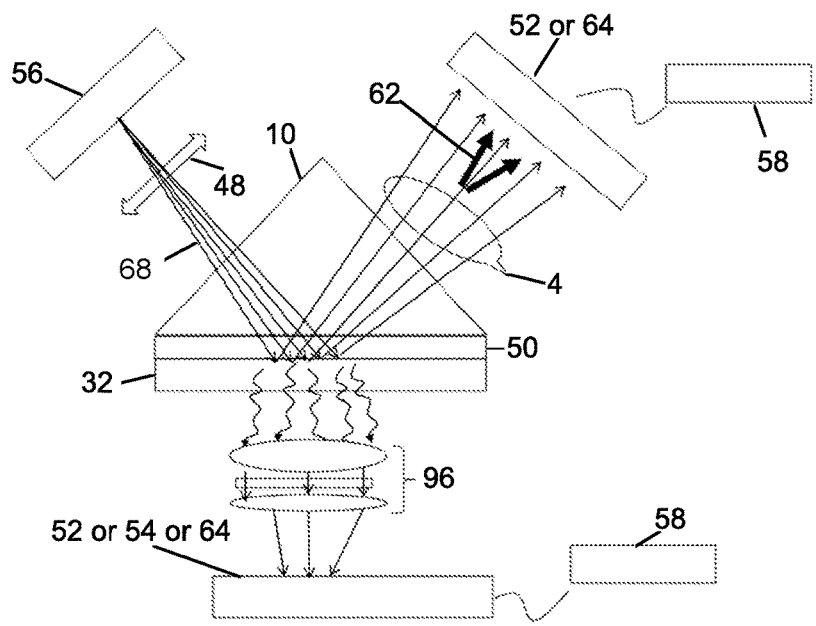
FIG. 18 schematically shows a combined system for diverging beam SPR and surface enhanced spectroscopy.

Enhanced Spectroscopy Combined with SPR:

The electromagnetic field enhancement at the surface between the metal and the analyte, when the SP wave is excited as shown in FIG. 7, may be utilized also to enhance other optical spectroscopies such as surface enhanced fluorescence (SEF), surface enhanced Raman scattering (SERS), surface enhanced infrared absorption (SEIRA), second harmonic generation and other surface enhanced spectroscopies. Hence one of the aspects of this invention is to combine SPR sensing with such enhanced spectroscopies as schematically shown in FIG. 18. The setup in FIG. 18 is similar to that in FIG. 8b. The excitation light wavelength should preferably be from a laser diverging so that the SP wave is excited on the surface near its central rays. Once the SP wave is excited a dark line is detected in the camera image while an enhanced emission signal is collected using a lens and filter system 96 from the other side of the prism and directed to a detector 52, a camera 64, or a spectrometer 54. The inventor of the present invention has found recently (see [211]) that in fact Ag films deposited with the GLAD technique having around 35% porosity give the highest SERS and SEF signal compared with the same type of films with different porosity. This fact, combined with the fact that with this porosity the SPR sensitivity is the optimum, a highly sensitive and reliable tool is obtained which combines SPR, SEF, SERS, SEIRA and other surface enhanced spectroscopies. The collection of the emitted light from the other side of the sensing surface (in FIG. 18 it is the prism surface, but it can also be used in the fiber or waveguide configurations as well) is done by collection or imaging optical components collected or imaged to the detector, camera or spectrometer. A filter is used to block the part of the exciting light that may be emitted in order to separate it from the frequency shifted light (fluorescence or Raman).

The surface enhanced spectroscopic modes may exhibit large enhancement factors particularly when the functionalized nanoparticles embedded within the analyte are made of noble metals. When these metallic nanoparticles arrive close enough to the plasmonic multilayered structure then an LSPR is excited on their surface which causes large local enhancement of the electromagnetic field. Hence with this configuration one gets both a large enhancement of the spectroscopic signals and also the sensitivity of the SPR sensor.

Another embodiment of a combined sensor is one in which the multilayered plasmonic structure is deposited on a transparent piezoelectric substrate 98 such as quartz, lithium niobate, or Polyvinylidene fluoride (PVDF) and the metal layer acts as an electrode to excite an acoustic wave in the piezoelectric transducer. This combination allows measuring concentrations of analytes using the piezo crystal microbalance (QCM) by measuring its resonant frequency shift in parallel to the SPR, and the surface enhanced spectroscopy signals. The scheme of the plasmonic/piezoelectric substrate is shown schematically in FIG. 19 in which only the substrate is drawn, the coupling medium (can be prism, waveguide or fiber) and index matching layer 100 between the substrate and the coupling medium 102 can be as described herein above.

Figure 19:
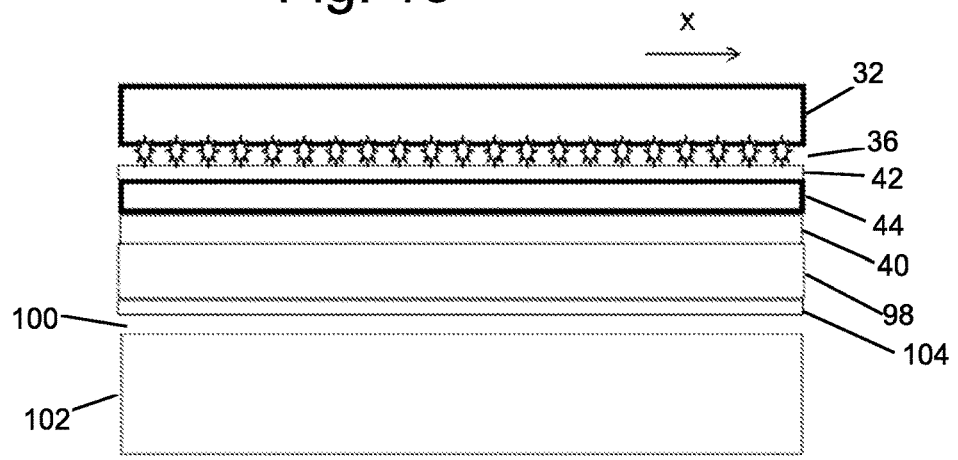
FIG. 19 schematically shows a sensor substrate made of a transparent piezoelectric material sandwiched between the plasmonic multilayered structure in which the metal layer is acting as the top electrode and a transparent bottom electrode.

The structure shown in FIG. 19 comprises—from the top down: analyte layer 32, functionalization layer 36, top nano layer 42, porous metal layer 32 that also acts as the top electrode, buried dielectric layer 40, the transparent piezoelectric substrate 98, and bottom transparent electrode 104.

Figure 20:
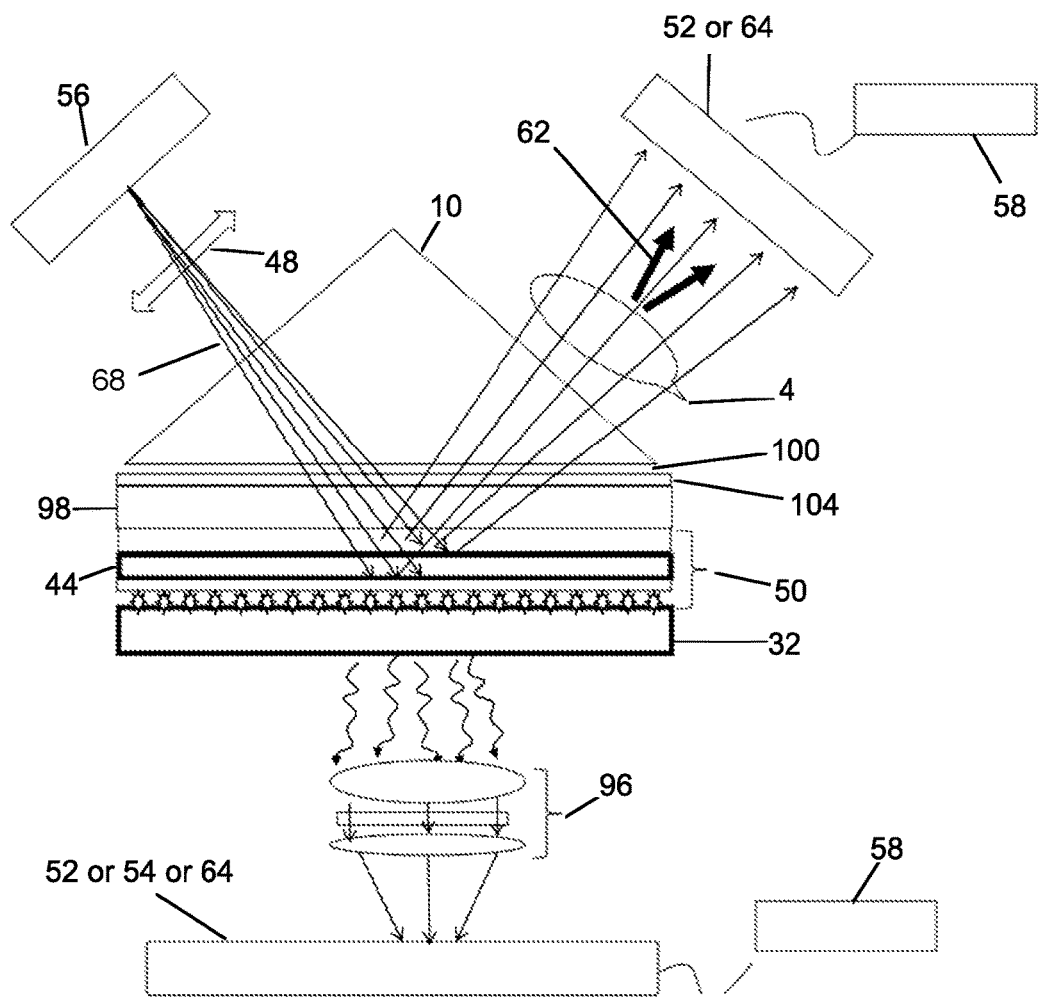
FIG. 20 schematically shows a combined system for multi-sensing including diverging beam SPR, surface enhanced spectroscopy and crystal microbalance.

A scheme that combines SPR with QCM and surface enhanced spectroscopy is depicted in FIG. 20. In this scheme the top electrodes can be the metallic plasmonic layer or alternatively the top Si layer or alternatively a transparent electrode layer such as indium tin oxide (ITO) on top of the metal or on top of the Si layer. The collection/imaging optics for the enhanced spectroscopy include lenses, spectral filters, apertures or polarizers as necessary for obtaining the signal with the best signal to noise ratio.

In the embodiment of the setup shown in FIG. 20 a 1D diverging beam 68 from light source 56 passes through polarizer 48 and prism 10, index matching fluid layer 100, transparent electrode 104 and transparent piezoelectric substrate 98 and is reflected from multilayered structure 50, which comprises a porous metal layer 44 that acts as the top electrode. The reflected beam 4 falls on a detector array 52 or camera 64. The output of the detecting device is sent to a processor and display unit 58. The dark region in the reflected beam where the dips appear is symbolically shown by bold arrows 62. The diverging beam SPR module can include additional components depending on whether the polarimetric/ellipsometric measurement is required as per the descriptions of FIG. 11 and FIG. 12 above. From the other side of the prism an enhanced emission signal is collected using a lens and filter system 96 and directed to a detector 52, a camera 64, or a spectrometer 54.

Another importance application of the SPR diverging beam methods described herein is making displacement and surface profiling measurements. Assuming the diverging beam is reflected from a vibrating surface then its mean direction will be shifting and changing due to the vibration. This diverging beam is now used as the source beam to excite the SPR on the structures described by this invention. As a result of the displacements, the dark line corresponding to the SPR will shift. Similarly the mean direction of the incident diverging beam can change upon movement of a surface with topography or tilted surface so that from the dark line shift the tilt angle or topography can be measured. The surface to be inspected can also be the mirror on top of an atomic force microscope (AFM) tip and the diverging beam shift will be enhanced by the well-known optical levering or triangulation effect. Another important application of the present invention is in autofocusing or surface profilometry with a microscope objective or lens system. Assuming that a light beam is focused on a surface to a spot with large enough diameter so that the reflected beam will be slightly diverging, then part of this reflected beam or all of it is directed towards the SPR sensor and the prism angle is adjusted such that the SPR occurs for rays not in the center but preferably near the edge of the light cone. As the surface is defocused then the rays that experience the SPR will shift and as a result the dark line shifts. Hence the dark line shift can be used for dynamic focusing control and for surface topography with high resolution. A calibration procedure is proposed herein in which the dark line position versus the surface displacement or topography change is saved in a database and used at later time to find the surface displacement.

Although embodiments of the invention have been described by way of illustration, it will be understood that the invention may be carried out with many variations, modifications, and adaptations, without exceeding the scope of the claims.

BIBLIOGRAPHY

1. Heinz Raether, Surface Plasmons on Smooth and Rough Surfaces and on Gratings, Springer Verlag 1988.
2. For recent review article on SFR imaging see: K. D. Kihm, "Surface plasmon resonance reflectance imaging technique for near-field (~100 nm) fluidic characterization" Experiments in Fluids 48, 547-564 (2010).
3. M. Zourob, S. Elwary, A. Turner, A. D. Taylor, J. Ladd, J. Homola, and S. Jiang, "Surface Plasmon Resonance (SPR) Sensors for the Detection of Bacterial Pathogens," in *Principles of Bacteria/Detection: Biosensors, Recognition Receptors and Microsystems* (Springer N.Y., 2008), pp. 83-108.
4. R. B. M. Schasfoort, and A. J. Tudos, eds. *Handbook of Surface Plasmon Resonance* (Royal Society of Chemistry, Cambridge, 2008).
5. A. Karabchevsky, S. Karabchevsky, and I. Abdulhalim, Fast surface plasmon resonance imaging sensor using Radon transform, Sensors and Actuators B: Chemical, 155, 361-365 (2011).
6. A. Karabchevsky, S. Karabchevsky, and I. Abdulhalim, Nano-precision algorithm for surface plasmon resonance determination from images with low contrast for improved sensor resolution, J. NanoPhotonics, 5, 051813-12 (2011). DOI: 10.1117/1.3598138.
7. Amit Lahav, Mark Auslender and I. Abdulhalim, Sensitivity enhancement of guided wave surface plasmon resonance sensors, Opt. Lett. 33, 2539-2541 (2008).
8. Amit Lahav, Atef Shalabney, I. Abdulhalim, Surface plasmon resonance sensor with enhanced sensitivity using nano-top dielectric layer, Journal of Nano-photonics 3, 031501 (2009).
9. Atef Shalabney and I. Abdulhalim, Figure of merit enhancement of surface plasmon resonance sensors in the spectral interrogation, Optics Letters 37, 1175 (2012).
10. Atef Shalabney, C. Khare, B. Rauschenbach, and I. Abdulhalim, Sensitivity of surface plasmon resonance sensors based on metallic columnar thin films in the spectral and angular interrogations, Sensors and Actuators B: Chemical, 159, 201-212 (2011).
11. Y. Y. Shevchenko and J. Albert, "Plasmon resonances in gold-coated tilted fiber Bragg gratings," Opt. Lett. 32, 211-213 (2007).
12. T. Allsop, R. Neal, S. Rehman, D. J. Webb, D. Mapps, and I. Bennion, "Generation of infrared surface plasmon resonances with high refractive index sensitivity utilizing tilted fiber Bragg gratings," Opt. Express 17, 16505-16517(2007).
13. L. Shao, Y. Shevchenko, and J. Albert, "Intrinsic temperature sensitivity of tilted fiber Bragg grating based surface plasmon resonance sensors," Opt. Express 18, 11464-11471 (2010).
14. C. Caucheteur, Y. Shevchenko, L. Shao, M. Wuilpart, and J. Albert, "High resolution interrogation of tilted fiber grating SPR sensors from polarization properties measurement," Opt. Express 19, 1656-1664 (2011).
15. Valerie Voisin, Christophe Caucheteur, Patrice Megret, and Jacques Albert, "Interrogation technique for TFBG-SPR refractometers based on differential orthogonal light states," Applied Optics 50, 4257-4261 (2011).
16. U.S. Pat. No. 2009/0263072, Jaques Albert et al., "Tilted Grating Sensor, (equivalent to WO 2008/049187 A1).
17. I. Abdulhalim,—Analytic propagation matrix method for linear optics of arbitrary biaxial layered media, J. Opt. A, 1 (5) (646-653) 1999).
18. U.S. Pat. No. 4,844,613, Batchelder et al., "Optical Surface Plasmon Sensor Device.
19. U.S. Pat. No. 6,801,317, Hofmann, A., "Plasmon Resonance Sensor".
20. O. Aharon, I. Abdulhalim, Liquid crystal wavelength independent continuous polarization rotator, Optical Engineering 49, 034002-4p (2010).
21. I. Abdulhalim, Plasmonic Sensing using Metallic Nano-Sculptured Thin Films, *Invited review article*, Small, 2014, DOI: 10.1002/smll.201303181.

The invention claimed is:

1. A sensor comprised of a multilayered plasmonic structure comprising a nano-porous metallic layer;
   a buried dielectric layer under the nanoporous metallic layer;
   a nano dimensional dielectric layer on top of the nanoporous metallic layer;
   a molecular layer for bio-functionalization on the interface of the multilayered structure with an analyte; and
   wherein the optical thickness of the nano dimensional dielectric layer is less than the cutoff for exciting guided modes in the nano dimensional dielectric layer.

2. The sensor of claim 1 wherein the thermo-optic coefficient of the buried dielectric layer is the same as that of material to be sensed.

3. A method of using the sensor of claim 1 to:
   i) determine the refractive index of a material; or
   ii) determine the presence and quantity of biological or chemical entities in thin film form or in an analyte; or
   iii) make displacement and surface profiling measurements; or
   iv) measure defocusing of an optical system;
the method comprising:
   a) providing an optical setup adapted to irradiate the analyte covered sensor of claim 1 with an input beam comprising TM polarized light;
   b) measuring the resonance wavelength or incidence angle of the resonant reflection dips of the plasmon excited at the plasmonic structure-analyte interface relative to the resonance wavelength or to the incidence angle of the resonant reflection dips of the plasmon excited at the buried dielectric layer metallic layer interface or relative to a reference material layer residing on top of the sensor—analyte interface and occupying part of its surface.

4. The method of claim 3, wherein the optical setup comprises one of the following:
   i) a quasi-monochromatic light source;
   ii) a wideband light source;
   iii) a multiple color light source; and
   iv) a tunable light source is adapted to provide quasi monochromatic light at multiple wavelengths serially.

5. The method of claim 3, wherein the optical setup comprises one of the following:
   i) means to obtain a uniform one dimensionally diverging beam in the plane of incidence of the input beam; and
   ii) means to obtain a uniform collimated beam in the plane of incidence of the input beam.

6. The method of claim 3, wherein the analyte is provided in a multichannel planar structure comprised of at least two rectangular channels, each channel having a width of at least twice the plasmon propagation length and a height of at least few times the penetration depth of the electromagnetic field, wherein the channels are oriented so that the line perpendicular to the channels is perpendicular to the plane of incidence of the input beam and wherein channels containing the analyte to be inspected are separated by channels containing a material having a thermo-optic coefficient similar to that of the analyte.

7. The method of claim 6, wherein each channel is coated with a different top nano dimensionally thick dielectric layer of different refractive index or different thickness.

8. The method of claim 6 in which the analyte is contained between the multilayered plasmonic structure and another transparent cover substrate coated with a transparent electrode, thereby allowing an electric field to be applied between the transparent electrode and the nano-porous metallic layer to help drag the species to be sensed towards the bio-functionalization layer.

9. The method of claim 6 in which the analyte comprises functionalized nanoparticles adapted to specifically attract the species to be detected and to bring them closer to the multilayered plasmonic structure.

10. The method of claim 9 in which the functionalized nanoparticles are magnetic, thereby allowing an external magnetic field to drag them towards the multilayered plasmonic structure.

11. The method of claim 9 in which the functionalized nanoparticles are metallic, thereby a localized plasmon is excited on their surface when they approach the plasmonic multilayered structure thus enhancing emission and the SPR sensor sensitivity.

12. The method of claim 3, wherein the optical setup comprises a prism, the multilayer plasmonic structure of the sensor of claim 1 is created either directly on a face of the prism or is created on a transparent substrate that is attached to the prism, and the analyte to be inspected covers the sensor.

13. The method of claim 12, wherein the optical setup comprises one of the following arrangements:
   i) a collimated wideband beam of light from a light source passes through a polarizer oriented along the TM direction, is incident on and passes through the prism, is reflected from the multilayered structure of the sensor, and the reflected beam passes through the prism towards a detector, an array of detectors, or a spectrometer;
   ii) a quasi-monochromatic one dimensionally diverging beam of light from a light source passes through a polarizer oriented along the TM direction, is incident on and passes through the prism, is reflected from the multilayered structure of the sensor, and the reflected beam passes through the prism towards a detector, an array of detectors, or a camera; and
   iii) a quasi-monochromatic one dimensionally diverging beam of light from a light source passes through a first dichroic mirror, passes through a polarizer oriented along the TM direction, is incident on and passes through the prism, is reflected from the multilayered structure of the sensor, and the reflected beam passes through the prism and a second dichroic mirror towards a detector, an array of detectors, or a camera; and, simultaneously, a collimated wideband beam of light from a light source is reflected from the first dichroic mirror, passes through the same polarizer oriented along the TM direction, is incident on and passes through the prism, is reflected from the multilayered structure of the sensor, and the reflected beam passes through the prism and is reflected from the second dichroic mirror towards a detector, an array of detectors, or a spectrometer.

14. The method of claim 13, wherein the optical setup comprises a quasi-monochromatic diverging beam of light from a light source that passes through a polarizer oriented along the TM direction, is incident on and passes through the prism, is reflected from a first side of the multilayered structure of the sensor; the reflected beam passes through the prism towards a detector, an array of detectors, or a camera; and an enhanced emission is transmitted through the analyte and is collected using a lens and filter system from a second side of the multilayered structure of the sensor and is directed towards a second detector, a second array of detectors, a second camera, or a spectrometer.

15. The method of claim 14, wherein the multilayered plasmonic structure of the sensor of claim 1 is deposited on one side of a transparent piezoelectric substrate, the nano-porous metallic layer acts as electrode to excite an acoustic wave in the piezoelectric transducer, a transparent electrode is deposited on the other side of the transparent piezoelectric substrate, and the prism, a waveguide, or an optical fiber coupling medium is attached using an index matching medium.

16. The method of claim 12, wherein the optical setup comprises a light source which produces a quasi-monochromatic one dimensionally diverging input beam of light that passes through a polarizer, is incident on and passes through the prism, is reflected from the multilayered structure of the sensor, and the reflected beam passes through the prism and at least one additional optical component towards at least one camera; wherein the polarizer is oriented at 45 degrees thereby generating equally polarized TE and TM components of the input beam; and
wherein the at least one additional optical component located between the prism and the at least one camera comprises one of the following:
   i) a polarized beam splitter, which directs each of the polarization components TE and TM to a different camera;
   ii) an analyzer; and
   iii) two non-polarizing beam splitters that direct the output beams to three different cameras and either three analyzers oriented at $-\pi/4$, $0$, $\pi/4$ degrees respectively or three analyzers oriented at −45 degrees and three passive waveplates providing phase retardations 0, $\pi/2$, $\pi$, respectively.

17. The method of claim 3, wherein the input beam is coupled to the sensor of claim 1 by means of one of the following:
  i) a waveguide created on a substrate, wherein the multilayered plasmonic structure of the sensor is created on top of the waveguide;
  ii) a transparent substrate that acts as a light pipe, wherein the multilayered plasmonic structure of the sensor is created on top of the transparent substrate;
  iii) an optical fiber, wherein a portion of the core of the optical fiber is exposed by removal of the cladding and the multilayered plasmonic structure of the sensor is created directly on the side of the fiber over that portion; and
  iv) an optical fiber comprising a tilted fiber grating wherein the multilayered plasmonic structure of the sensor is created on the cladding of the fiber directly over the grating.

18. The method of claim 17, wherein the input beam is reflected from a first side of the multilayered structure of the sensor towards a detector, an array of detectors, or a camera and an enhanced emission is transmitted through the analyte and is collected using a lens and filter system from a second side of the multilayered structure of the sensor and is directed towards a second detector, a second array of detectors, a second camera, or a spectrometer.

\* \* \* \* \*